(12) United States Patent
Tada et al.

(10) Patent No.: US 11,000,304 B2
(45) Date of Patent: May 11, 2021

(54) MEDICAL DEVICE AND TREATMENT METHOD

(71) Applicant: TERUMO KABUSHIKI KAISHA, Tokyo (JP)

(72) Inventors: Yuichi Tada, Kanagawa (JP); Yuki Itoh, Kanagawa (JP); Kosuke Nishio, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 190 days.

(21) Appl. No.: 15/998,406

(22) Filed: Aug. 15, 2018

(65) Prior Publication Data

US 2018/0353199 A1 Dec. 13, 2018

Related U.S. Application Data

(63) Continuation of application No. PCT/JP2017/005377, filed on Feb. 14, 2017.

(30) Foreign Application Priority Data

Feb. 15, 2016 (JP) .............................. JP2016-026336

(51) Int. Cl.
*A61B 17/32* (2006.01)
*A61B 90/00* (2016.01)
(Continued)

(52) U.S. Cl.
CPC ............... *A61B 17/32002* (2013.01); *A61B 17/320758* (2013.01); *A61B 90/03* (2016.02); *A61B 2017/00398* (2013.01); *A61B 2017/00685* (2013.01); *A61B 2017/22071* (2013.01); *A61B 2017/320024* (2013.01);
(Continued)

(58) Field of Classification Search
CPC ................. A61B 17/320758; A61B 2017/320766–320775; A61B 90/03; A61B 2090/031–036
See application file for complete search history.

(56) References Cited

U.S. PATENT DOCUMENTS 6,045,566 A    4/2000 Pagedas

FOREIGN PATENT DOCUMENTS

JP    2014533147 A    12/2014
JP    2015521903 A    8/2015

OTHER PUBLICATIONS

An English Translation of the International Search Report (Form PCT/ISA/210) and the Written Opinion of the International Searching Authority (Form PCT/ISA/237) dated May 23, 2017, by the Japanese Patent Office in corresponding International Application No. PCT/JP2017/005377. (5 pages).

*Primary Examiner* — Shaun L David
(74) *Attorney, Agent, or Firm* — Buchanan, Ingersoll & Rooney PC

(57) ABSTRACT

A medical device has a rotatable drive shaft, a rotary body that includes a cutting edge for applying a cutting force to a stenosed site, and that is disposed on a distal side of the drive shaft so as to be rotated in conjunction with rotation of the drive shaft, a switching portion whose distal end is disposed at a position protruding from the cutting edge, and a holding portion that holds the switching portion so as to move the switching portion on the same plane as the cutting edge or to a position away from the stenosed site beyond the cutting edge in accordance with a pushing force, when the switching portion is pushed against the stenosed site.

19 Claims, 23 Drawing Sheets

(51) Int. Cl.
*A61B 17/3207* (2006.01)
*A61B 17/00* (2006.01)
*A61B 17/22* (2006.01)

(52) U.S. Cl.
CPC .............. *A61B 2017/320032* (2013.01); *A61B 2017/320052* (2013.01); *A61B 2017/320733* (2013.01); *A61B 2017/320766* (2013.01); *A61B 2017/320775* (2013.01); *A61B 2090/036* (2016.02); *A61B 2090/08021* (2016.02); *A61B 2217/005* (2013.01)

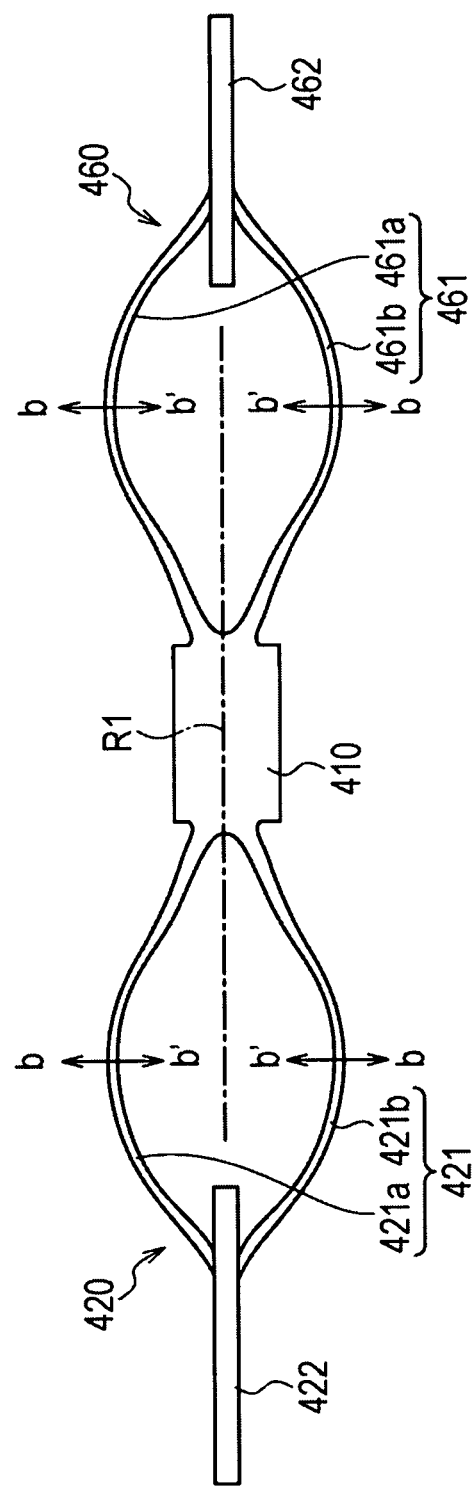

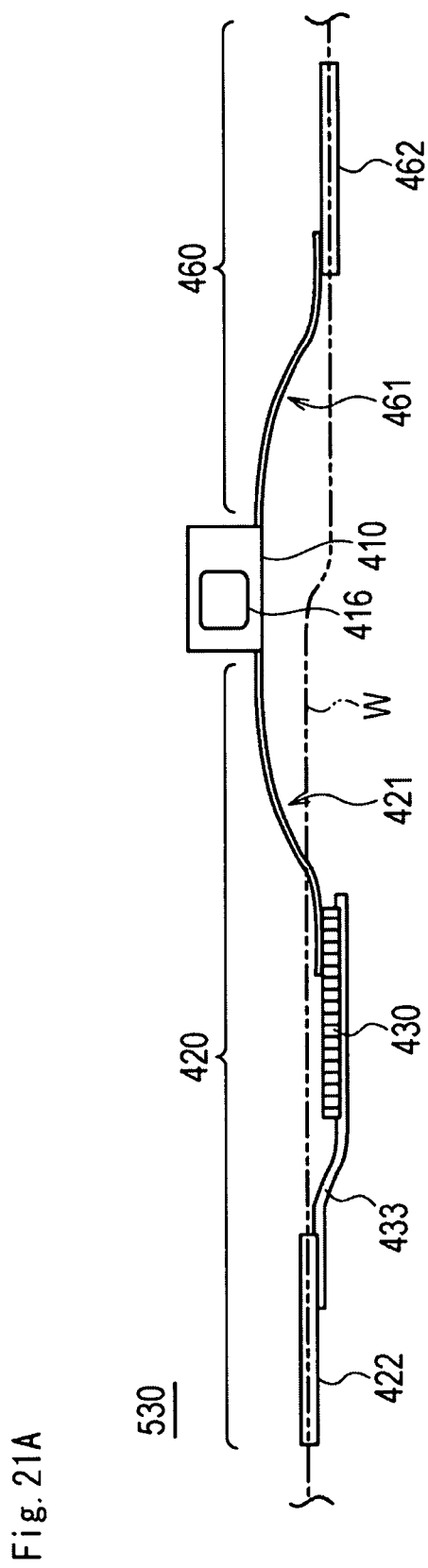

MEDICAL DEVICE AND TREATMENT METHOD

CROSS-REFERENCES TO RELATED APPLICATIONS

This application is a continuation of International Application No. PCT/JP2017/005377 filed on Feb. 14, 2017, which claims priority to Japanese Application No. 2016-026336 filed on Feb. 15, 2016, the entire contents of both being incorporated herein by reference.

TECHNICAL FIELD

The present invention relates to a medical device and a treatment method for cutting an object which is present inside a biological lumen.

BACKGROUND ART

Treatment using a balloon catheter or an indwelling technique of a stent has been used in the related art as a method of treating a stenosed site formed inside a blood vessel such as a coronary artery. However, a therapeutic effect is less likely to be obtained over a long period of time merely by using a balloon to widen a vascular lumen. It is known that stent indwelling causes a new stenosis. In addition, when a complicated lesion develops, as in a case where a plaque of the stenosed site is calcified and hardened, or in a case where the stenosed site appears in a branched portion of the blood vessel, the therapeutic effect cannot be sufficiently obtained merely by performing a treatment using a balloon catheter or stent.

On the other hand, as the treatment for extending patency of the blood vessel or for contributing to an improved treatment outcome in the complicated lesion, there is known atherectomy for extracorporeally removing an object such as a plaque, a calcified lesion, or a thrombus which may cause the stenosis.

As a medical device for the atherectomy, for example, JP-T-2014-533147 has proposed a medical device having a rotary body provided with a cutting edge (blade surface) for applying cutting force to the stenosed site disposed in a distal portion of an elongated catheter. In the treatment using this medical device, work for pushing the cutting edge against the stenosed site is carried out in a state where the rotary body is rotated.

It is desirable that the medical device used for the treatment of the stenosed site formed inside a biological lumen is provided with various functions which enable suitable treatment depending on a property, a size, a shape, or a forming site of the stenosed site. For example, in order that the medical device is suitable for the particular characteristics of an object (stenosed site) serving as a treatment target site, the medical device is provided with the ability to selectively switch the state of the cutting edge. In this manner, not only it is possible to smoothly and quickly perform a medical procedure, but also it is possible to improve the therapeutic effect.

However, the medical device disclosed in JP-T-2014-533147 is not configured so that the distal portion (distally located end) having the cutting edge can be switched depending on the characteristics of the object serving as the treatment target site. Therefore, the treatment cannot be progressively performed while various functions of the medical device are switched therebetween during the medical procedure. For example, in a case where the treatment is performed by switching various functions therebetween, an operator has to temporarily remove the medical device out of a living body, replace the medical device itself with another medical device, or replace a member such as the rotary body. Consequently, the medical procedure takes a longer time, thereby increasing a burden on a patient.

The disclosure herein is made in view of the above-described problems, and aims to provide a medical device and a treatment method, in which a medical procedure can be smoothly and quickly performed and an improved therapeutic effect can be realized by enabling a state of a cutting edge to be switched while inside a biological lumen.

SUMMARY

According to the disclosure herein, there is provided a medical device for cutting an object inside a biological lumen. The medical device has a rotatable elongated member, a rotary body that includes a cutting edge for applying a cutting force to the object, and that is disposed on a distal side of the elongated member so as to be rotated in conjunction with rotation of the elongated member, a switching portion whose distal end is disposed at a position protruding from the cutting edge, and a holding portion that holds the switching portion so as to move the switching portion on the same plane as the cutting edge or to a position away from the object beyond the cutting edge in accordance with a pushing force, when the switching portion is pushed against the object.

In addition, according to the disclosure here, there is provided a treatment method for cutting an object inside a biological lumen. The treatment method has a movement step of bringing a switching portion into a state of protruding to a distal side of a rotary body including a cutting edge for applying a cutting force to the object, and pushing the switching portion against the object so as to move the switching portion on the same plane as the cutting edge or to a position away from the object beyond the cutting edge, and a cutting step of causing the cutting edge to cut the object in a state where the switching portion is moved.

According to the medical device in the disclosure here, a pushing force for pushing the switching portion against a predetermined object serving as a cutting target is adjustable. In this manner, a state of the cutting edge can be easily switched without taking out the medical device from the biological lumen. In this manner, it is possible to save labor needed to carry out work for switching the state of the cutting edge, and it is possible to smoothly and quickly perform a medical procedure. In addition, the treatment can be progressively performed while the state of the cutting edge is appropriately switched depending on the property of the object serving as the cutting target. Accordingly, it is possible to improve a therapeutic effect of the medical procedure using the medical device.

In the treatment method according to the disclosure herein, the state of the cutting edge is switched by adjusting the pushing force for pushing the switching portion against the predetermined object serving as the cutting target. In addition, the treatment can be progressively performed while the state of the cutting edge is appropriately switched depending on the property of the object serving as the cutting target. Therefore, according to the treatment method, the medical procedure can be smoothly and quickly performed, and the therapeutic effect can be improved.

BRIEF DESCRIPTION OF THE DRAWINGS

FIG. 15B is a bottom view of the distal member when viewed in a direction of an arrow 15B illustrated in FIG. 15A.

FIG. 21A is a view illustrating a distal member included in a medical device according to Modification Example 3 of the second exemplary embodiment.

DESCRIPTION OF EMBODIMENTS

Figure 1:
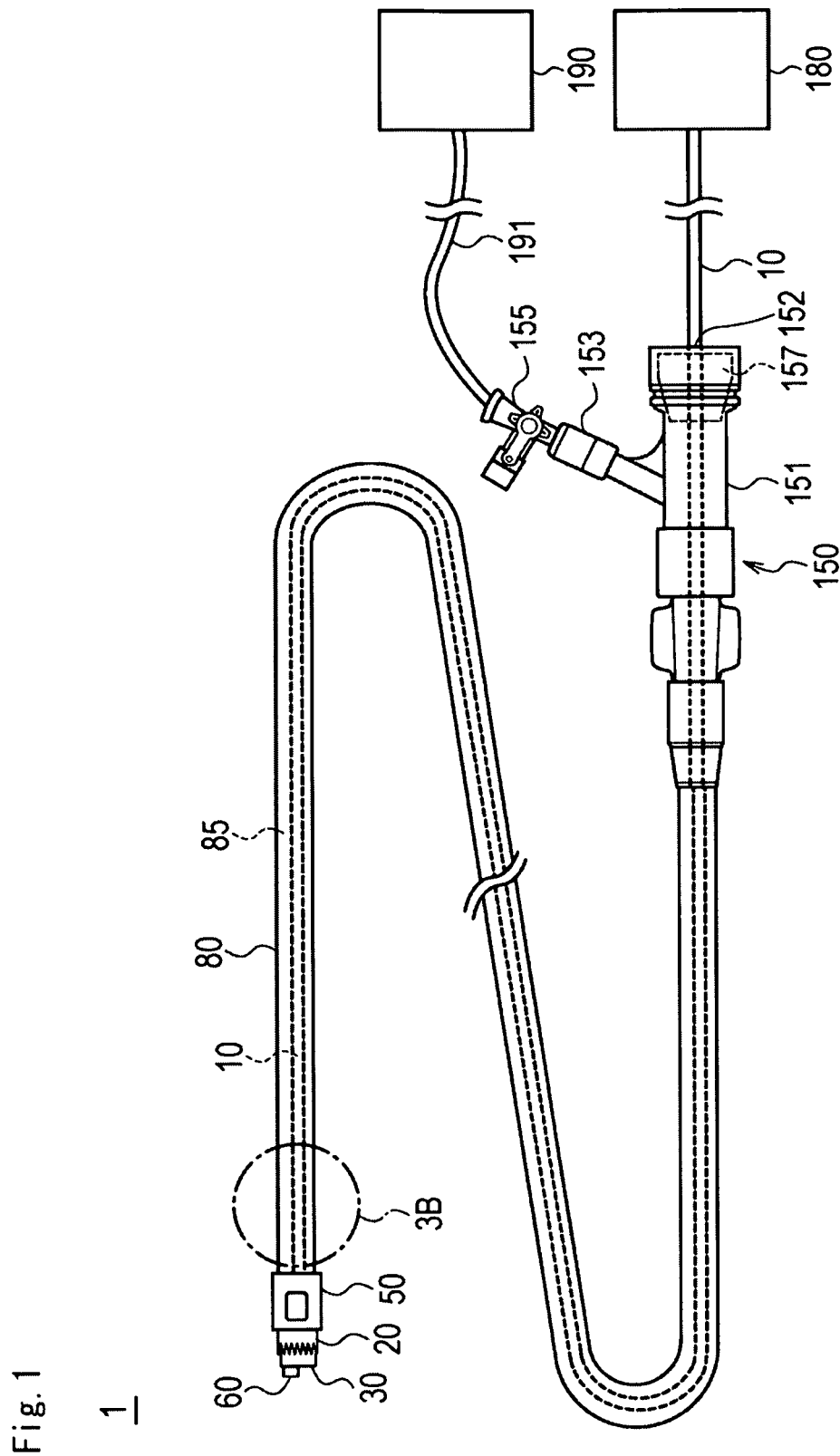
FIG. 1 is a plan view of a medical device according to a first exemplary embodiment of the disclosure.

Hereinafter, embodiments according to the disclosure will be described with reference to the drawings. Dimensional proportions in the drawings are exaggerated and different from actual proportions for convenience of description, in some cases.

First Embodiment

As illustrated in FIG. 4, a medical device 1 according to a first exemplary embodiment is used in treatment for cutting a stenosed site (object) S or an occluded site formed in a blood vessel H which is a biological lumen. In the description herein, a side inserted into the biological lumen in the medical device 1 will be referred to as a distal side (distally located side), and a side operated by a hand will be referred to as a proximal side (proximally located side).

Figure 2A:
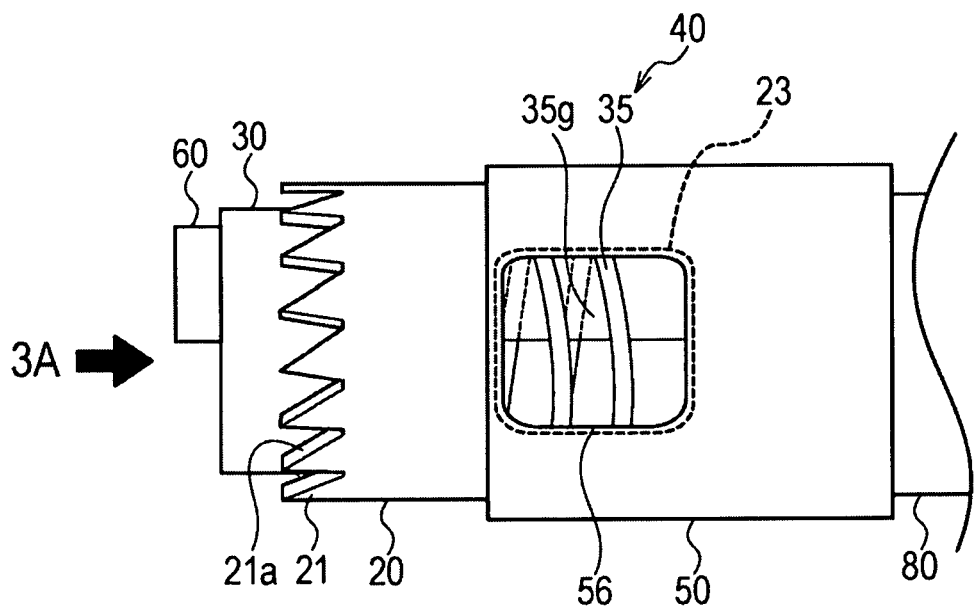
FIG. 2A is an enlarged view of a rotary body included in the medical device according to the first exemplary embodiment.
Figure 2B:
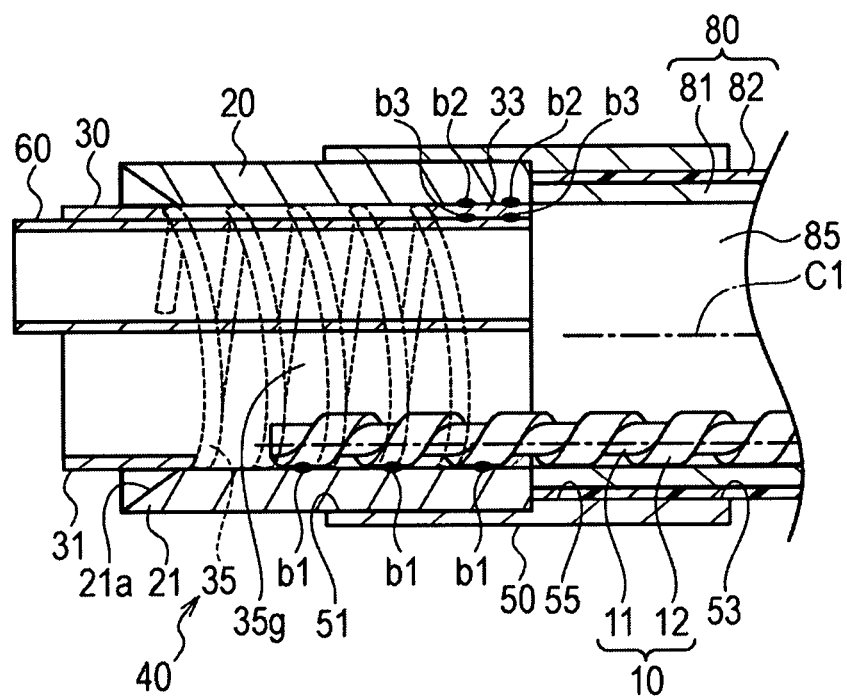
FIG. 2B is a cross-sectional view taken along an axial direction of the rotary body included in the medical device according to the first exemplary embodiment.

As illustrated in FIG. 1, the medical device 1 has an elongated tube (catheter) 80 which can be introduced into the biological lumen. As illustrated in FIGS. 2A and 2B, a distal portion of the tube 80 has a rotary body 20 including a cutting edge 21 for applying a cutting force to the stenosed site S, a switching portion 30 (protector) whose distal end is disposed at a position protruding from the cutting edge 21, a holding portion 40 that holds the switching portion 30 at a predetermined position, a rotation receiving portion (corresponding to a main body portion) 50 disposed on a proximal side of the rotary body 20, and a cutting assistance portion 60 that assists cutting performed by the cutting edge 21.

According to the first exemplary embodiment of the disclosure, the switching portion 30 is configured to serve as a protector that prevents the cutting edge 21 of the rotary body 20 from inadvertently coming into contact with a biological tissue other than the stenosed site S which is a treatment target site.

The rotary body 20 internally has a hollow cylindrical shape. The cutting edge 21 disposed on a distal end of the rotary body 20 is configured to include a sharp blade protruding toward the distal side. As illustrated in FIG. 2A, a side surface of the rotary body 20 has a side hole 23 through which an interior and an exterior of the rotary body 20 communicate with each other.

For example, the rotary body 20 can be configured to include a known metal material, a resin material, or ceramics provided with biocompatibility. For example, the metal material includes stainless steel, nickel titan (titanium alloy), tungsten, cobalt chromium, titan, and tungsten carbide. A surface of these metal materials is subjected to surface treatment such as nitriding treatment. In this manner, it is possible to use the metal material whose hardness at the surface is further improved over the base material. For example, the cutting edge 21 may be configured to include a multiple layer structure in which similar or dissimilar types of the metal are disposed in multiple layers. For example, as the resin material, it is possible to use BS (acrylonitrile, butadiene, and styrene copolymer synthetic resin), polyethylene, polypropylene, nylon, PEEK, polycarbonate, acrylic, polyacetal, modified polyphenylene ether, acrylonitrile styrene, or those which have improved strength by allowing these resin materials to contain additives such as glass fibers.

The cutting edge 21 included in the rotary body 20 has a blade surface 21a cut in an uneven shape (saw-tooth shape). The blade surface 21a is disposed along a circumferential direction of the rotary body 20. In the blade surface 21a included in the cutting edge 21, a shape, a thickness, a length, and a material are not particularly limited, as long as the cutting force can be applied to the stenosed site S. However, in a case where the blade surface 21a has a saw-tooth shape as in the cutting edge 21, it is possible to finely crush the stenosed site S. Therefore, the stenosed site S can be efficiently cut.

As illustrated in FIGS. 1 and 26, the rotary body 20 is disposed on the distal side of a rotationally driven drive shaft (corresponding to an elongated member) 10. The rotary body 20 is rotated in conjunction with rotation of the drive shaft 10.

As illustrated in FIG. 2B, the drive shaft 10 has a core (core bar) 11 and a reinforcement body 12 fixed to the core 11. For example, the core 11 can be formed of a known metal material such as stainless steel. The reinforcement body 12 can be formed of those which are obtained by spirally machining the known metal material such as the stainless steel. The reinforcement body 12 can be fixedly attached to an outer surface of the core 11 by using a known method such as bonding using an adhesive and soldering.

As illustrated in FIG. 2B, a distal portion of the drive shaft 10 is fixed to an inner surface of the rotary body 20 via a plurality of fixing portions b1. The distal portion of the drive shaft 10 is fixed to the inner surface of the rotary body 20, and is disposed at a position which is eccentric outward from a central axis Cl of the tube 80. Fixing at the fixing portion b1 can be performed by a method of bonding using an adhesive, welding, or melting, for example.

As illustrated in FIG. 1, a proximal portion of the drive shaft 10 is configured to be connectable to an external drive apparatus 180 via a predetermined connector (not illustrated). The external drive apparatus 180 includes a drive source configured to include a known electric motor which generates a rotational force for rotating the drive shaft 10. If the rotational force generated by the external drive apparatus 180 is applied to the drive shaft 10, the rotational force is transmitted from the proximal side to the distal side of the drive shaft 10, thereby rotating the rotary body 20 disposed in the distal portion of the drive shaft 10. If the rotary body 20 is rotated, the cutting edge 21 disposed in the distal end of the rotary body 20 can apply the cutting force to the stenosed site S (refer to FIG. 4B).

The external drive apparatus 180 and an aspiration device 190 (to be described later) can be controlled by a control unit (not illustrated), for example. For example, as the control unit, it is possible to use those which are configured to include a known microcomputer having a CPU, a RAM, and a ROM. In addition, for example, the control unit may be installed in the external drive apparatus 180 or the aspiration device 190, or may be incorporated in a device separate from the external drive apparatus 180 or the aspiration device 190. In this way, a control signal may be transmitted and received between the apparatus 180 and the device 190 in a wire or wireless manner.

As illustrated in FIG. 1, a hand operation unit 150 is disposed in the proximal portion of the tube 80. The hand operation unit 150 has a hub 151, a connector portion 153 disposed in the hub 151, and a port 155 disposed in the connector portion 153.

For example, the connector portion 153 can be configured to include a Y-connector known in a medical field. A three-way plug for controlling circulation of a fluid inside and outside the port 155 is disposed in the port 155. For example, the port 155 can interlock with the aspiration device 190 via the tube 191 through which the fluid can be circulated. For example, the aspiration device 190 can be configured to include a known fluid aspiration pump which can generate negative pressure.

Figure 3A:
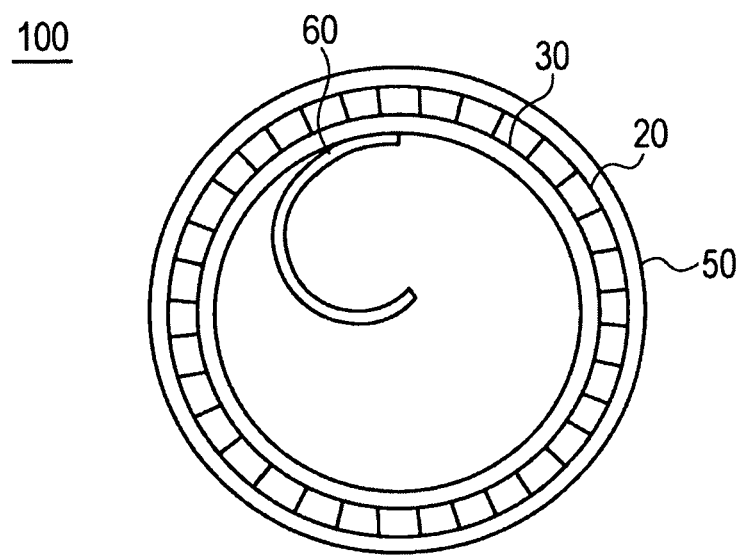
FIG. 3A is a front view of the rotary body when viewed in a direction of an arrow 3A illustrated in FIG. 2.
Figure 3B:
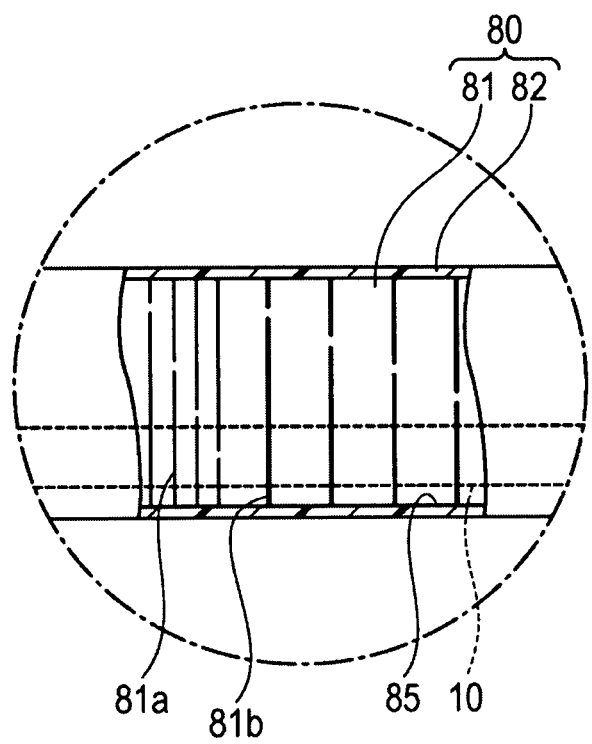
FIG. 3B is an enlarged cross-sectional view of a portion surrounded by a single-dot chain line 3B illustrated in FIG. 1.

As illustrated in FIGS. 2B and 3B, the tube 80 includes a lumen 85 extending in an extending direction of the tube 80. The lumen 85 communicates with an interior of the hub 151. The drive shaft 10 is inserted into the lumen 85 of the tube 80. As illustrated in FIG. 2B, a distal portion of the drive shaft 10 is fixed to the rotary body 20. In addition, as illustrated in FIG. 1, the proximal side of the drive shaft 10 is inserted into the lumen 85 and the hub 151 of the tube 80, and is pulled out from a proximal end port 152 of the hub 151. The proximal portion of the hub 151 has a valve body 157 for preventing the fluid from leaking out of the proximal end port 152.

In a case where the medical device 1 is delivered using a guide wire when the medical device 1 is introduced into the biological lumen, for example, the guide wire can be inserted into the lumen 85 of the tube 80. In addition, for example, the valve body 157 or the hub 151 can appropriately have a port for pulling out the guide wire from the proximal end of the medical device 1 without interfering with the drive shaft 10.

A structure or a material of the elongated member which transmits a drive force to the rotary body 20 is not particularly limited, as long as the rotational drive force can be transmitted from the proximal side to the distal side of the elongated member (from the hand operation unit 150 side to the rotary body 20 side). The elongated member may be any member other than the drive shaft 10. For example, the elongated member can be formed of a resin material. In a case where the elongated member is formed of the resin material, for example, it is possible to use a resin-made tube configured to include a single layer or multiple layers, or those which are obtained by adding a reinforcement member such as a blade to the resin-made tube. In addition, for example, as the elongated member, it is also possible to use a metal pipe subjected to spiral machining, a tightly wound coil spring, and those which are obtained by coating these members with the resin-made tube.

As illustrated in FIGS. 2A and 2B, the protector (switching portion) 30 has a hollow distal portion 31 which protrudes to the distal side beyond the cutting edge 21 of the rotary body 20 in the state where an external force is not applied from the outside, a hollow proximal portion 33 which is fixed to the proximal portion of the rotary body 20, and a stretchable and deformable portion 35 which extends between the distal portion 31 and the proximal portion 33.

The stretchable and deformable portion 35 is configured to include a hollow coil spring which is stretchable along an extending direction (rightward-leftward direction in FIG. 2B) of the rotation receiving portion 50. The coil spring configuring the stretchable and deformable portion 35 has a gap 35g disposed at a predetermined interval in the extending direction.

The stretchable and deformable portion 35 has a function to serve as the holding portion 40 for holding a position of the protector 30 and changing the position of the protector 30. According to the first exemplary embodiment, the protector 30 is configured to include the distal portion of the holding portion 40 (stretchable and deformable portion 35). That is, the holding portion 40 and the protector 30 are integrally formed from a single member.

For example, the protector 30 and the holding portion 40 (stretchable and deformable portion 35 can be configured to include a known metal material or resin material provided with biocompatibility. For example, the holding portion 40 can also be configured to include a member separate from the protector 30. In addition, a material or a structure of the holding portion 40 is not particularly limited, as long as the holding portion 40 is stretchable and deformable. The holding portion 40 can also be configured to include an elastically deformable member such as a plate spring, resin rubber, sponge, and a spring obtained by spirally machining a metal pipe.

The proximal portion of the protector 30 is fixed to the inner surface of the rotary body 20 via a fixing portion b2. Fixing in the fixing portion b2 can be performed by a method of bonding using an adhesive, welding, or melting, for example.

The protector 30 prevents the cutting edge 21 from coming into contact with the biological tissue other than the stenosed site S in a state where the protector 30 protrudes from the cutting edge 21. The holding portion 40 holds the protector 30 (distal portion 31 of the protector 30) so as to move the protector 30 on the same plane as the cutting edge 21 or to a position away from the stenosed site S beyond the cutting edge 21 in accordance with the pushing force, when the protector 30 is pushed against the stenosed site S (refer to FIG. 5A). If the protector 30 moves on the same plane as the cutting edge 21 or to the position away from the stenosed site S beyond the cutting edge 21, the cutting edge 21 is in brought into a state of being in contact with the stenosed site S. Accordingly, the cutting force can be applied to the stenosed site S. That is, the protector 30 has a function to reversibly switch the cutting edge 21 between a first orientation (state) which can prevent the cutting edge 21 from coming into contact with the biological tissue and a second orientation (state) which enables the cutting edge 21 to cut the stenosed site S.

The above description of "switching" does not only mean switching between the state of enabling the cutting edge 21 to cut the stenosed site S and the state of preventing the cutting edge 21 from coming into contact with the biological tissue, but also means switching between influences of cutting edge 21 on the biological tissue and the stenosed site S. For example, as will be described in modification examples (to be described later), switching the state of enabling the cutting edge 21 itself to cut the stenosed site S and the state of enabling a member other than the cutting edge 21 to cut the stenosed site S is also included in the above description of "switching".

The protector 30 can be configured to protrude 0.5 mm from the cutting edge 21, for example, in a state where no load is applied from the outside. In addition, in a case where the protector 30 is moved to a position away from the stenosed site S beyond the cutting edge 21 by being pushed against the stenosed site S, for example, the protector 30 can be configured to be located 0.3 mm away from the cutting edge 21. These dimensions are only examples, and the exemplary embodiment is not particularly limited to these dimensions.

As illustrated in FIGS. 2A and 2B, the rotation receiving portion 50 has a distal opening portion 51, a proximal opening portion 53, a lumen 55 linked between the distal opening portion 51 and the proximal opening portion 53, and a side hole 56 disposed on the side surface.

An inner surface on the distal side of the rotation receiving portion 50 is provided with a stepped portion whose tube wall thickness is thinner than the other portions. The proximal portion of the rotary body 20 is inserted into the stepped portion.

An arrangement or a fixing structure of the rotary body 20 and the tube 80 inside the rotation receiving portion 50 can be appropriately changed. For example, the stepped portion may not be disposed in the rotation receiving portion 50. The tube 80 may be inserted into the rotation receiving portion 50, and the tube 80 may narrow the inner diameter of the rotation receiving portion 50 so as to provide the stepped portion. In this manner, the rotary body 20 may be inserted into the stepped portion.

The interior of the rotary body 20 and the lumen 55 of the rotation receiving portion 50 communicate with each other. If the rotary body 20 is rotated and the side hole 56 of the rotation receiving portion 50 is disposed at a position overlapping the side hole 23 of the rotary body 20, a portion of the gap 35g disposed in the stretchable and deformable portion 35 is exposed outward (state illustrated in FIG. 2A).

When the rotary body 20 is rotated, the proximal portion of the rotary body 20 is supported by the inner surface of the rotation receiving portion 50. The proximal portion of the rotary body 20 is thus supported by the rotation receiving portion 50. In this manner, the rotary shaft of the rotary body 20 is stabilized. Accordingly, the rotary body 20 is smoothly rotated. The rotation receiving portion 50 is not fixed to the rotary body 20. Accordingly, the rotation receiving portion 50 is not rotated when the rotary body 20 is rotated.

The distal end of the tube 80 is inserted into the proximal side of the rotation receiving portion 50. The distal end (distal end of the outer layer 82) of the tube 80 is fixed to the inner surface of the rotation receiving portion 50. The tube 80 and the rotary body 20 can be fixed to each other by a method of bonding using an adhesive, welding, or melting, for example.

As illustrated in FIG. 3B, the tube 80 has a tube main body 81 and an outer layer 82 for covering the tube main body 81.

At least one first slit 81a is disposed on the distal side of the tube main body 81, and at least one second slit 81b is disposed on the proximal side of the first slit 81a. The first slit 81a has a smaller slit interval than the second slit 81b. The first slit 81a is disposed on the distal side of the tube main body 81. Accordingly, the distal side can be curved with a relatively large curvature. On the other hand, the second slit 81b is disposed on the proximal side of the tube main body 81. Accordingly, the proximal side can be curved with a relatively small curvature. For example, the tube main body 81 can be configured to include a known metal material or a hard resin material.

In the outer layer 82, the material of the tube 80 is allowed to be more flexible. Furthermore, when the biological tissue and the tube 80 come into contact with each other, the outer layer 82 protects the biological tissue. In addition, the outer layer 82 prevents a debris D flowing into the tube 80 from being discharged from the tube 80. For example, as the outer layer 82, it is possible to use a hollow tube configured to include a known resin material such as polyethylene, polypropylene, and polyamide.

As illustrated in FIG. 2B, the cutting assistance portion 60 is disposed so that the distal end protrudes from the distal end of the protector 30 and the proximal end is fixed to the proximal portion of the holding portion 40. The proximal end of the cutting assistance portion 60 is fixed to the inner surface of the holding portion 40 via the fixing portion b3. Fixing at the fixing portion b3 can be performed by a method of bonding using an adhesive, welding, or melting, for example. The proximal end of the cutting assistance portion 60 is fixed at a position on the proximal side beyond the stretchable and deformable portion 35 of the protector 30. Accordingly, when the cutting assistance portion 60 is pushed against the stenosed site S, it is possible to prevent an excessive force from being applied to the stretchable and deformable portion 35. In this manner, it is possible to preferably prevent damage to the stretchable and deformable portion 35.

The cutting assistance portion 60 has a hollow shape. In addition, as illustrated in FIG. 3A, in a front view, the cutting assistance portion 60 has a substantially U-shape which has a cutout portion formed in a portion in the circumferential direction. In the medical device 1 according to the first exemplary embodiment, the cutting assistance portion 60 is disposed so as to protrude from the distal portion 31 of the protector 30 regardless of the stretchable deformation (deformation in the axial direction) of the holding portion 40. Therefore, in order to prevent the biological tissue from being inadvertently damaged by the cutting assistance portion 60, it is preferable to configure the cutting assistance portion 60 so as to have a shape which can minimize the cutting force, compared to the cutting edge 21 of the rotary body 20 including the blade surface 21a having a saw-tooth shape.

A shape or a size of the cutting assistance portion 60, and a positional relationship between the cutting assistance portion 60 and the protector 30 are not limited to the illustrated examples, and can be appropriately changed. For example, the cutting assistance portion having a solid structure can be used, or the shape or the arrangement can be changed so as to be capable of preventing interference with the guide wire inserted into the rotary body 20.

As illustrated in FIG. 2B, the cutting assistance portion 60 is indirectly fixed to the rotary body 20 via the proximal portion (proximal portion 33 of the protector 30) of the holding portion 40. If the rotary body 20 is rotated, the holding portion 40 is rotated in conjunction with the rotation of the rotary body 20, and the cutting assistance portion 60 is also rotated. When the cutting is performed, prior to the cutting edge 21, the cutting assistance portion 60 enters the inside of the stenosed site S serving as the cutting target, and forms a cutout portion inside the stenosed site S. If the cutting edge 21 of the rotary body 20 is pushed against the stenosed site S in a state where the cutout portion is formed, the stenosed site S can be more easily cut, compared to a case where no cutout portion is formed. In addition, if the cutting edge 21 is pushed against the stenosed site S in a state where the cutting assistance portion 60 enters the inside of the stenosed site S, the cutting assistance portion 60 supports the rotary body 20 with respect to the stenosed site S. Accordingly, misalignment of the rotary shaft of the rotary body 20 is suppressed. In this manner, particularly in a case where the stenosed site S serving as the treatment target site is a calcified lesion, the cutting can be efficiently performed using the cutting edge 21 of the rotary body 20.

Next, referring to FIGS. 4A to 4C, 5A, and 5B, a treatment method using the medical device 1 will be described. Herein, a method of cutting the stenosed site S formed in the blood vessel H will be described as an example.

Figure 4A:
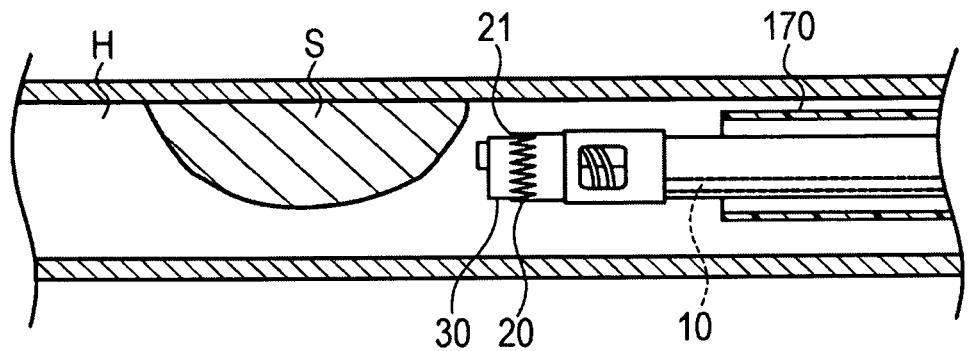
FIG. 4A is a cross-sectional view schematically illustrating a treatment example using the medical device according to the first exemplary embodiment.

First, as illustrated in FIG. 4A, a guiding sheath 170 is introduced to the vicinity of the stenosed site S. The guiding sheath 170 can be delivered to the vicinity of the stenosed site S along a guide wire (not illustrated) introduced before the guiding sheath 170 is introduced. When the guiding sheath 170 is delivered, using the guide wire may be appropriately omitted.

Next, the medical device 1 is delivered to the vicinity of the stenosed site S via the guiding sheath 170. In this case, the medical device 1 can be delivered along the guide wire by inserting the guide wire into the hub 151, the tube 80, the protector 30, and the holding portion 40. While the medical device 1 is delivered to the vicinity of the stenosed site S, the medical device 1 is in a state where the external force is not applied to the protector 30 and the holding portion 40. Accordingly, as illustrated in FIGS. 2A and 2B, the protector 30 is in a state of protruding from the cutting edge 21 of the rotary body 20. Therefore, it is possible to prevent the cutting edge 21 from inadvertently coming into contact with a normal biological tissue of the vascular wall.

Figure 4B:
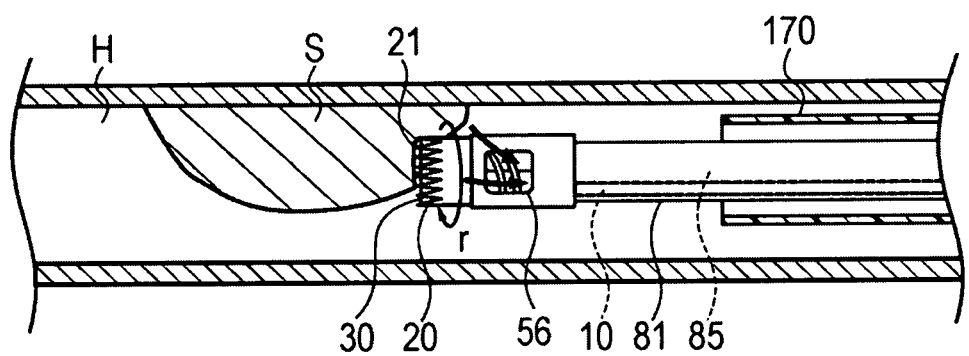
FIG. 4B is a cross-sectional view schematically illustrating a treatment example using the medical device according to the first exemplary embodiment.
Figure 5A:
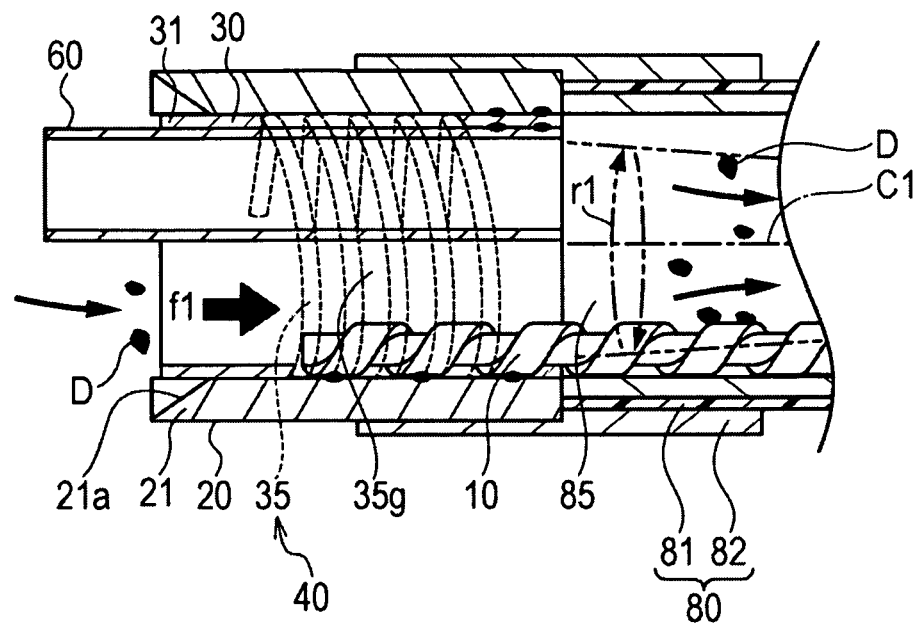
FIG. 5A is a view for describing an operation of the medical device according to the first exemplary embodiment.

Next, as illustrated in FIG. 4B, while the rotary body 20 is rotated as indicated by an arrow r, the medical device 1 is pushed against the stenosed site S from the distal side. As illustrated in FIG. 5A, if a pushing force f1 is added toward the proximal side by pushing the protector 30 against the stenosed site S, the pushing force f1 is transmitted to the holding portion 40 holding the protector 30, and the holding portion 40 is contracted to the proximal side. If the holding portion 40 is contracted, the protector 30 moves so as to be drawn into the rotary body 20. Then, the distal end of the protector 30 moves on the same plane as the cutting edge 21 or to the position away from the stenosed site S beyond the cutting edge 21. If the cutting edge 21 is brought into a state of protruding from the distal side beyond the protector 30, the cutting force can be applied from the cutting edge 21 to the stenosed site S. Accordingly, a stenosed substance (for example, a plaque or a thrombus) of the stenosed site S can be cut off.

When the stenosed substance of the stenosed site S is cut by rotating the cutting edge 21, for example, the aspiration device 190 illustrated in FIG. 1 is operated. In this manner, the cut stenosed substance (debris) D can be aspirated into the rotary body 20. The debris D flows into the rotary body 20 by way of the distal opening portion of the rotary body 20, and flows toward the proximal side by way of the tube 80 which communicates with the proximal side of the rotary body 20. In this manner, the debris D is collected by the aspiration device 190. In this case, an aspirating force of aspirating the debris D into the rotary body 20 is increased by a convection flow induced by the rotation of the rotary body 20. Accordingly, the debris D smoothly moves toward the interior of the rotary body 20.

Figure 5B:
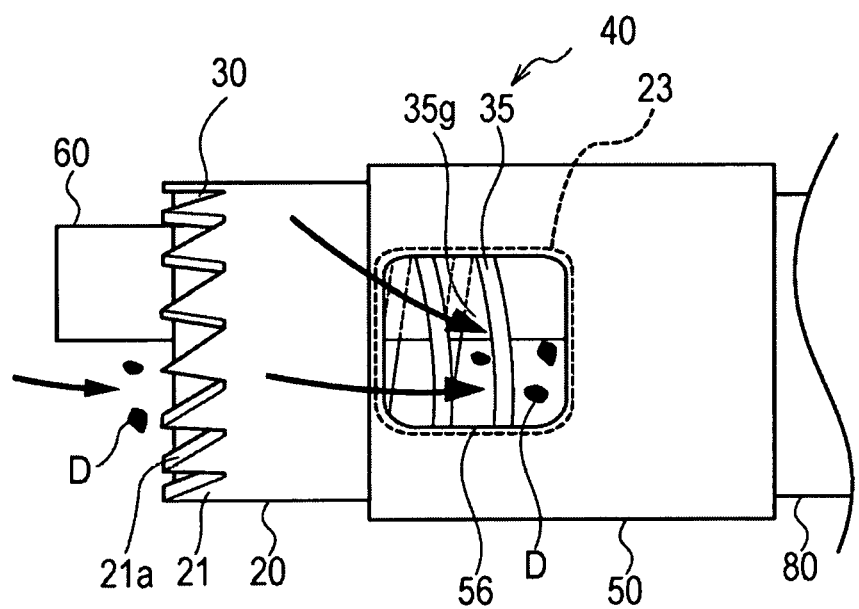
FIG. 5B is a view for describing an operation of the medical device according to the first exemplary embodiment.

In addition, as illustrated in FIG. 5B, the debris D is aspirated into the protector 30 by way of the side hole 56 disposed in the rotation receiving portion 50, the side hole 23 disposed in the rotary body 20, and the gap 35g disposed in the stretchable and deformable portion 35. The debris D is aspirated from the distal side of the rotary body 20 and the side surface side of the protector 30. In this manner, the debris D can be efficiently collected, and it is possible to prevent the debris D as a cutting scrap from being accumulated around the rotary body 20. Therefore, it is possible to prevent the debris D from sticking to the cutting edge 21 of the rotary body 20, and it is possible to increase the cutting force applied to the stenosed site S by the cutting edge 21.

When the stenosed site S is cut by the rotary body 20, while the cutting assistance portion 60 is rotated in conjunction with the rotary body 20, the cutting force is applied to the stenosed site S on the distal side beyond the rotary body 20. In the stenosed site S, a portion to which the cutting force is applied by the rotary body 20 is in a state of being cut in advance by the cutting assistance portion 60. Therefore, in a portion with which the cutting edge 21 of the rotary body 20 comes into contact, the stenosed site S is brittle. Accordingly, it is possible to prevent the rotation of the rotary body 20 from being hindered due to the contact, and the cutting can be smoothly and progressively performed by the rotary body 20. For example, even in a case where the stenosed site S is formed to be relatively rigid, the cutting edge 21 of the rotary body 20 is brought into contact with a portion in which auxiliary cutting is performed by the cutting assistance portion 60. Accordingly, the cutting force can be sufficiently applied to the stenosed site S.

As illustrated in FIG. 5A, when the drive shaft 10 is rotated, a rotary shaft thereof is displaced to a position eccentric from the central axis Cl of the tube 80. The reason that the rotary shaft is displaced to the eccentric position in this way is that the drive shaft 10 is fixed to the inner surface of the rotary body 20 located on the outer periphery beyond from the central axis Cl of the tube 80. A rotational orbit of the drive shaft 10 is an elliptical orbit indicated by an arrow r1. While the drive shaft 10 is rotated by drawing the elliptical orbit, the drive shaft 10 applies a shear force to the debris D flowing into the rotary body 20 and into the tube 80. The debris D is finely crushed by the applied shear force. Since the debris D is crushed, it is possible to prevent clogging of the debris D inside the rotary body 20 and inside the tube 80. Then, it is possible to smoothly move the debris D to the proximal side of the tube 80 by preventing the aspirating force from being weakened due to the clogging of the debris D. The drive shaft 10 is inserted along the extending direction of the lumen 85 of the tube 80. Accordingly, the shear force can be applied to the debris D at various locations in the extension direction of the tube 80. Therefore, the debris D is more finely crushed as the debris D flows to the proximal side. Accordingly, even in a case where a relatively large amount of the debris D is aspirated into the tube 80 within a short period of time, it is possible to preferably prevent clogging by the debris D.

Figure 4C:
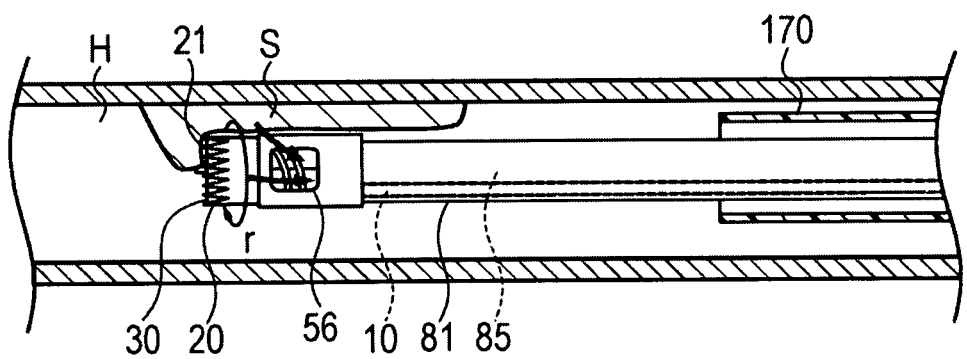
FIG. 4C is a cross-sectional view schematically illustrating a treatment example using the medical device according to the first exemplary embodiment.

As illustrated in FIG. 4C, the medical device 1 is moved to the distal side so that the cutting edge 21 of the rotary body 20 is pushed against the stenosed site S. Through this work, the stenosed site S can be cut along the extending direction. After it is confirmed that the cutting treatment is completely performed on the stenosed site S, the medical device 1 is appropriately removed from the living body. It is also possible to subsequently perform the cutting treatment on the other stenosed site S.

As described above, the medical device 1 according to the first exemplary embodiment includes the rotatable drive shaft 10 and a cutting edge 21 for applying the cutting force to the stenosed site S, and has the rotary body 20 disposed on the distal side of the drive shaft 10 and rotated in conjunction with the drive shaft 10, the switching portion 30 whose distal end is disposed at the position protruding from the cutting edge 21, and the holding portion 40 that holds the switching portion 30 so as to move the switching portion 30 on the same plane as the cutting edge 21 or to the position away from the stenosed site S beyond the cutting edge 21 in accordance with the pushing force, when the switching portion 30 is pushed against the stenosed site S.

According to the medical device 1 configured as described above, the pushing force for pushing the switching portion 30 against the stenosed site S serving as the cutting target is adjusted. In this manner, the property of the cutting edge 21 can be easily switched without taking out the medical device 1 from the blood vessel H. In this manner, it is possible to save labor needed to carry out work for switching the state of the cutting edge 21, and it is possible to smoothly and quickly perform the medical procedure. In addition, the treatment can be progressively performed while the state of the cutting edge 21 is appropriately switched depending on the property of the stenosed site S. Accordingly, it is possible to improve the therapeutic effect of the medical procedure using the medical device 1.

In addition, in a case where the switching portion 30 is configured to serve as the protector 30 for protecting the cutting edge 21, the pushing force for pushing the protector 30 against the stenosed site S serving as the cutting target is adjusted. In this manner, it is possible to reversibly switch between the state where the protector 30 protrudes from the cutting edge 21 of the rotary body 20 and the state where the protector 30 moves on the same plane as the cutting edge 21 or to the position away from the stenosed site S beyond the cutting edge 21. When the protector 30 is brought into a state of protruding from the cutting edge 21, it is possible to prevent the cutting edge 21 from inadvertently coming into contact with the biological tissue (for example, a normal biological tissue) other than the stenosed site. Accordingly, when performing the treatment, an operator does not have to pay extra attention to the treatment. In this manner, the quick treatment can be realized, and the burden felt by a patient due to the treatment can be reduced.

The rotation receiving portion 50 having the lumen 55 for communicating with the interior of the rotary body 20 is disposed in the proximal end of the rotary body 20. The holding portion 40 is configured to be stretchable and deformable along the extending direction of the rotation receiving portion 50. Therefore, the holding portion 40 is stretched and deformed in conjunction with the operation for pushing the protector 30 against the stenosed site S and the operation for releasing the pushed state. In this manner, the protector 30 can be reversibly moved to the position protruding from the cutting edge 21, and on the same plane as the cutting edge 21 or the position away from the stenosed site S beyond the cutting edge 21.

In addition, the rotation receiving portion 50 has a tubular shape including the distal opening portion 51, the proximal opening portion 53, and the lumen 55 linked to the distal opening portion 51 and the proximal opening portion 53. At least a portion of the holding portion 40 is inserted into the rotation receiving portion 50. The protector 30 is configured to be movable in the inward-outward direction (axial direction) of the rotation receiving portion 50 by the stretchable deformation of the holding portion 40. Therefore, the protector 30 can be moved into and out of the rotation receiving portion 50 in conjunction with the stretchable deformation of the holding portion 40. The protruding amount of the protector 30 protruding from the rotation receiving portion 50 is thus adjustable. In this manner, it is possible to switch between the state where the cutting can be performed by the cutting edge 21 of the rotary body 20 and the state where the cutting performed by the cutting edge 21 is limited.

In addition, the holding portion 40 is configured to include a hollow spring 35, and the protector 30 is integrally disposed in the distal portion of the holding portion 40. Therefore, the holding portion 40 can be easily moved by elastically deforming the spring 35. In addition, the protector 30 and the holding portion 40 are disposed integrally with each other. In this manner, it is possible to minimize an increase in the number of components. Accordingly, it is possible to reduce the manufacturing cost.

In addition, the side surface of the rotation receiving portion 50 has the side hole 56 through which the interior of the holding portion 40 and the exterior of the rotation receiving portion 50 communicate with each other. Therefore, the debris D generated when the stenosed site S is cut can be efficiently collected into the holding portion 40. Accordingly, it is possible to prevent the cutting force from being weakened due to the generated debris D.

In addition, the medical device 1 further includes the cutting assistance portion 60 disposed in the rotary body 20 so as to assist the cutting performed by the cutting edge 21. The distal side of the cutting assistance portion 60 is disposed so as to protrude from the distal end of the protector 30. The proximal side of the cutting assistance portion 60 is fixed to the proximal side of the holding portion 40. Therefore, the cutting efficiency of the stenosed site S can be improved by the cutting assistance portion 60.

In addition, the cutting edge 21 included in the rotary body 20 has the blade surface 21a which is cut in an uneven shape. Accordingly, the stenosed site S can be finely crushed. Even in a case where the stenosed site S serving as the treatment target site is a calcified lesion, the stenosed site S can be efficiently cut.

The treatment method according to the first exemplary embodiment includes bringing the switching portion 30 into a state of protruding to the distal side of the rotary body 20 including the cutting edge 21 for applying the cutting force to the stenosed site S and pushing the switching portion 30 against the stenosed site S so as to move the switching portion 30 on the same plane as the cutting edge 21 or to the position away from the stenosed site S beyond the cutting edge 21, and the step of causing the cutting edge 21 to cut the stenosed site S in a state where the switching portion 30 is moved.

According to the treatment method described above, the state of the cutting edge 21 is switched by adjusting the pushing force for pushing the switching portion 30 against the stenosed site S serving as the cutting target. The treatment can be progressively performed while the state of the cutting edge 21 is appropriately switched depending on the property or characteristics of the stenosed site S. Therefore, according to this method, the medical procedure can be smoothly and quickly performed, and the therapeutic effect can be improved.

In addition, the switching portion 30 is configured to include the protector 30, and the protector 30 is brought into a state of protruding from the cutting edge 21. In this manner, it is possible to prevent the cutting edge 21 from inadvertently coming into contact with the biological tissue other than the stenosed site S. Then, the protector 30 is pushed against the stenosed site S so as to move the cutting edge 21 on the same plane as the cutting edge 21 or to the position away from the object beyond the cutting edge 21. In this manner, the treatment can be performed using the cutting edge 21. According to this method, the operator does not have to pay extra attention to the treatment when the treatment is performed. Accordingly, the quick treatment can be realized, and the burden felt by the patient due to the treatment can be reduced.

In addition, the step of moving the protector 30 is performed in such a way that the holding portion 40 for holding the protector 30 is contracted and deformed along the extending direction of the rotation receiving portion 50 including the lumen 55 communicating with the interior of the rotary body 20. Therefore, the holding portion 40 can be stretched in conjunction with the operation for pushing the protector 30 against the stenosed site S and the operation for releasing the pushed state, and furthermore, the protector 30 can be reversibly moved.

In addition, at least a portion of the holding portion 40 is disposed inside the rotation receiving portion 50, and the protector 30 is configured to be movable in the inward-outward direction of the rotation receiving portion 50 by the stretchable deformation of the holding portion 40. Therefore, the protector 30 can be moved into and out of the rotation receiving portion 50 in conjunction with the stretchable deformation of the holding portion 40. The protruding amount of the protector 30 protruding from the rotation receiving portion 50 is adjustable. In this manner, it is possible to switch between the state where the cutting can be performed by the cutting edge 21 and the state where the cutting performed by the cutting edge 21 is limited.

In addition, the holding portion 40 is configured to include the hollow spring 35, and the protector 30 is integrally disposed in the distal portion of the holding portion 40. Therefore, the holding portion 40 can be easily moved by elastically deforming the spring 35. In addition, the protector 30 and the holding portion 40 are disposed integrally with each other. In this manner, it is possible to minimize an increase in the number of components. Accordingly, it is possible to reduce the manufacturing cost.

The above-described treatment method further has the step of introducing the cut debris D into the rotation receiving portion 50 and into the holding portion 40 via the side hole 56 disposed on the side surface of the rotation receiving portion 50. Therefore, the debris D generated when the stenosed site S is cut can be efficiently collected into the holding portion 40. In this manner, it is possible to prevent the cutting force from being weakened due to the generated debris D.

In addition, the cutting step includes the step of cutting the stenosed site S while the cutting edge 21 is assisted by the cutting assistance portion 60 disposed in the rotary body 20. Therefore, the cutting assistance portion 60 can assist the cutting of the stenosed site S, and the cutting edge 21 of the rotary body 20 can improve the cutting efficiency. In particular, in a case where the stenosed site S is progressively calcified and becomes harder, a cutting assistance function of the cutting assistance portion 60 is satisfactorily fulfilled.

Next, a medical device according to Modification Example 1 of the first exemplary embodiment will be described.

Figure 6:
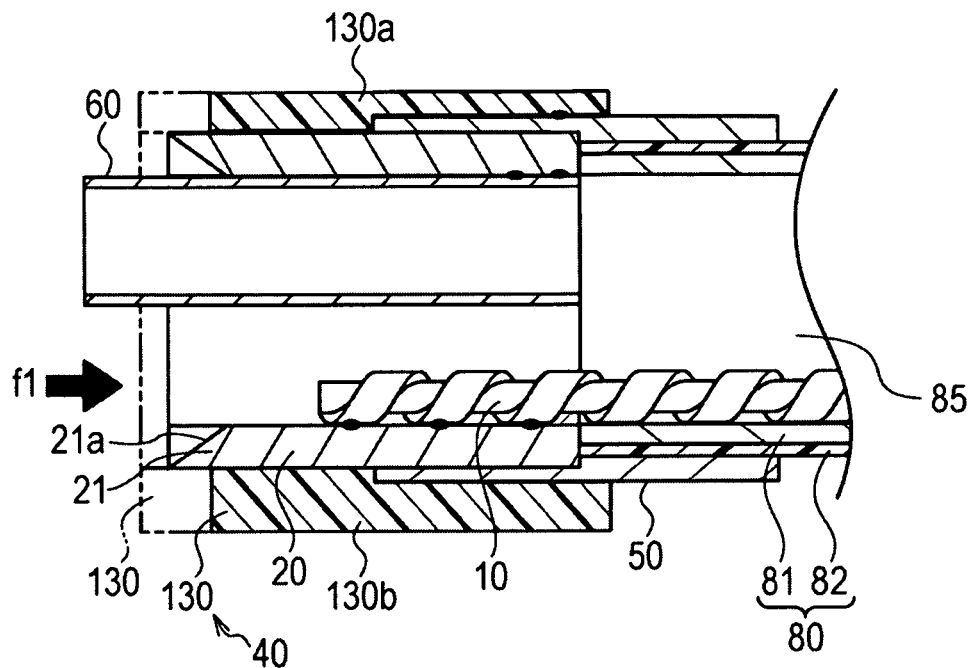
FIG. 6 is a cross-sectional view illustrating a medical device according to Modification Example 1 of the first exemplary embodiment.

As illustrated in FIG. 6, in this modification example, the protector 130 is disposed on the outer surface of the rotary body 20. The protector 130 is configured to include an elastic member having a substantially tubular shape. For example, as the elastic member, it is possible to use resin rubber, sponge, or elastically deformable metal.

The elastic member configuring the protector 130 also has a function to serve as the holding portion 40 for holding the protector 130.

For example, the proximal portion of the protector 130 can be fixed to the outer surface of the proximal portion of the rotation receiving portion 50. Fixing can be performed by a method of bonding using an adhesive, welding, or melting, for example. The protector 130 is not fixed to the rotary body 20. Accordingly, the rotary body 20 is not rotated in conjunction with the rotation of the rotary body 20.

The thickness of a portion of the protector 130 in the circumferential direction can be further thickened than other portions. In this modification example, for example, a portion 130b on a lower portion side (bottom surface side) in the circumferential direction is thicker than a portion 130a on an upper portion side. Compared to the thin portion 130a, the cutting force of the cutting edge 21 is less likely to act on the thick portion 130b of the protector 130, when the stenosed site S is cut, thereby suppressing the cutting. Therefore, the cutting is preferentially performed on the thin portion 130a side of the protector 130. Accordingly, a forward movement direction of the rotary body 20 is guided inward of the stenosed site S (outward when viewed from the center of the blood vessel). As a result, the cutting edge 21 of the rotary body 20 can be prevented from coming into contact with a portion (portion located on the lower side in FIGS. 4A to 4C) of the vascular wall located on a side facing the stenosed site S. Accordingly, it is possible to further improve the safety of the medical procedure.

In the protector 130, for example, if the thick portion 130b is disposed in at least a portion located on the vertically downward direction side when viewed from the central axis of the protector 130, on an axially orthogonal cross-section of the protector 130, a function of guiding the moving direction of the above-described rotary body 20 can be fulfilled. Therefore, determining which range is suitable for the arrangement is not particularly limited.

Next, a medical device according to Modification Example 2 of the first exemplary embodiment will be described.

Figure 7:
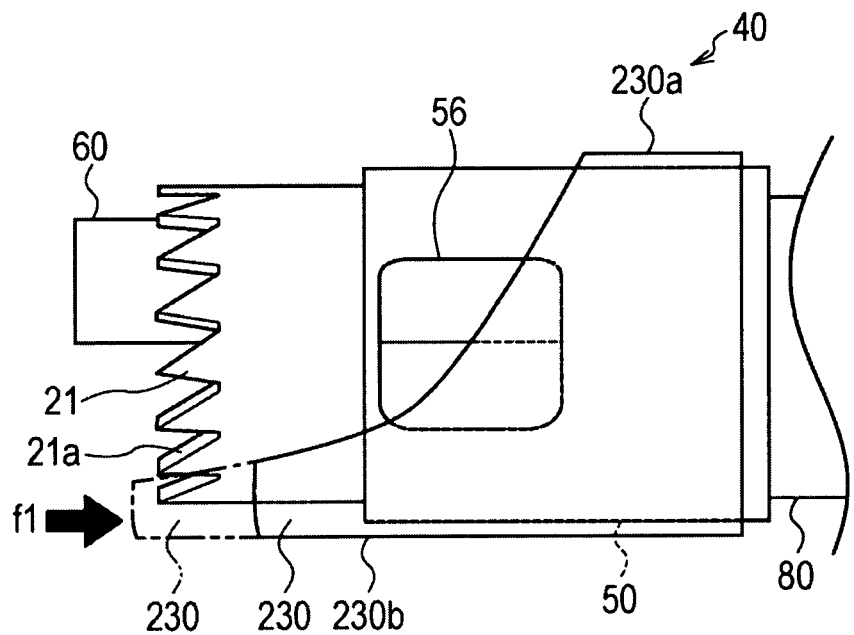
FIG. 7 is a cross-sectional view illustrating a medical device according to Modification Example 2 of the first exemplary embodiment.

As illustrated in FIG. 7, in this modification example, the protector 230 is configured to include the elastic member which can be externally mounted on the outer surface of the rotation receiving portion 50. For example, as the elastic member, it is possible to use resin rubber, sponge, or elastically deformable metal.

The protector 230 internally has a hollow shape, and is externally mounted so as to cover the proximal portion of the rotation receiving portion 50. The protector 230 has an inclined cutout portion which externally exposes a portion of the side hole 56 of the rotation receiving portion 50, in a state where the protector 230 is externally mounted on the rotation receiving portion 50. The bottom portion 230b located in the distal end of the protector 230 extends to the distal side. The bottom portion 230b has a function to prevent the cutting edge 21 of the rotary body 20 from coming into contact with the biological tissue other than the stenosed site S. The proximal end of the protector 230 has a function to serve as the holding portion 40 which holds the protector 230 with respect to the rotation receiving portion 50.

The protector 230 is not fixed to the rotary body 20. Accordingly, the protector 230 is not rotated in conjunction with the rotation of the rotary body 20.

In the distal portion of the protector 230, only the bottom portion 230b side protrudes. Therefore, when the stenosed site S is cut, the bottom portion 230b comes into contact with the stenosed site S. When the cutting is performed by the cutting edge 21 of the rotary body 20, similar to Modification Example 1 described above, the cutting is thereby suppressed on the bottom portion 230b side. Accordingly, the forward movement direction of the rotary body 20 is guided inward of the stenosed site S (outward when viewed from the center of the blood vessel). Therefore, the cutting edge 21 of the rotary body 20 can be prevented from coming into contact with the portion of the vascular wall located on the side facing the stenosed site S. Accordingly, it is possible to further improve the safety of the medical procedure.

As described above with reference to Modification Examples 1 and 2, the structure of the protector and the holding portion can prevent the cutting edge disposed on the distal end of the rotary body from inadvertently coming into contact with a site other than the stenosed site (object). A specific configuration is not particularly limited, as long as the protector and the holding portion are pushed against the object so as to be switched to a state where the cutting edge can come into contact with the object.

Next, a medical device according to Modification Example 3 of the first exemplary embodiment will be described.

Figure 8:
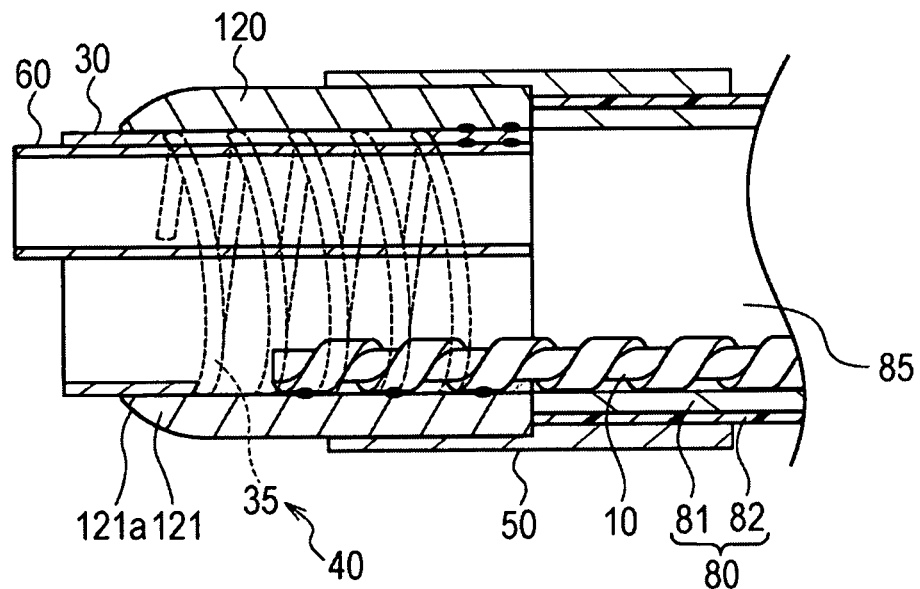
FIG. 8 is a cross-sectional view illustrating a medical device according to Modification Example 3 of the first exemplary embodiment.

As illustrated in FIG. 8, in this modification example, a cutting edge 121 of a rotary body 120 is provided with a tapered blade surface 121a whose thickness is thinned toward the distal side of the rotary body 120.

For example, the blade surface 121a can have a shape the same as that of a trepanned blade surface (blade surface having a tapered shape toward the distal side and having the smooth distal surface) used for a biopsy device in the medical field. The cutting edge 121 includes the blade surface 121a. In this manner, when the stenosed site S is cut, the blade surface 121a is pushed against the stenosed site S while being rotated. Accordingly, the blade surface 121a can smoothly enter the inside of the stenosed site S, and the cutting force can be applied so as to cut off the stenosed site S. In this manner, even in a case where the stenosed site S is a soft tissue, the cutting of the stenosed site S can be efficiently performed.

Next, a medical device according to Modification Example 4 of the first exemplary embodiment will be described.

Figure 9:
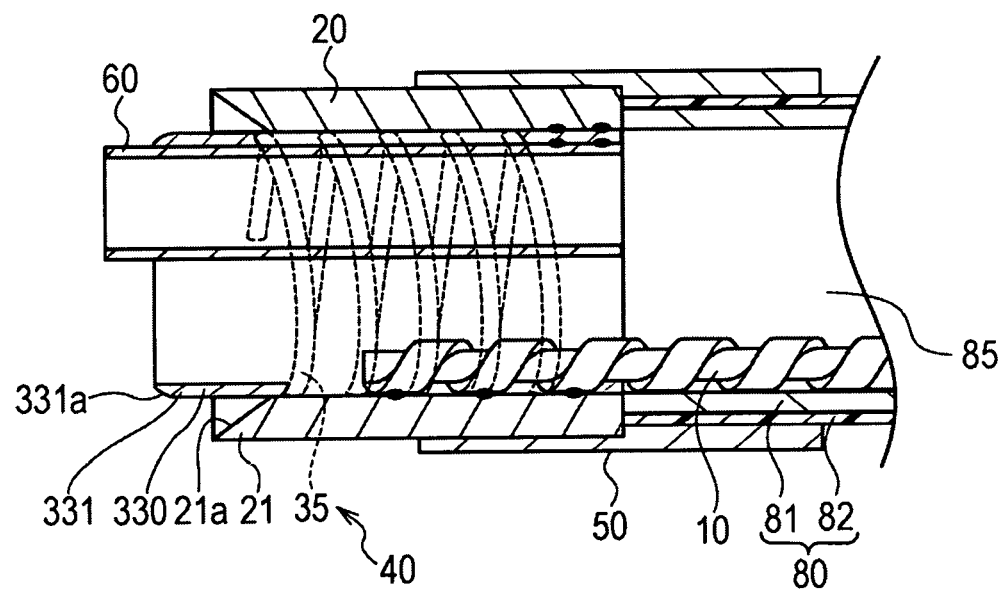
FIG. 9 is a cross-sectional view illustrating a medical device according to Modification Example 4 of the first exemplary embodiment.

As illustrated in FIG. 9, in this modification example, the distal end of the switching portion 330 is provided with a cutting portion 331 which applies the cutting force to the stenosed site S. The cutting portion 331 is disposed in the switching portion 330. Accordingly, the stenosed site S can be cut by pushing the switching portion 330 against the stenosed site S.

For example, in a state where the switching portion 330 is pushed against the stenosed site S by using a slightly weaker pushing force, the cutting can be performed using the cutting portion 331. The pushing force applied to the stenosed site S is then increased so that the switching portion 330 moves rearward to the proximal side. In this manner, the cutting can be performed using the cutting edge 21 of the rotary body 20. That is, in this modification example, the switching portion 330 has a function to switch between the state where the cutting is performed using the cutting edge 21 of the rotary body 20 and the state where the cutting is performed using the cutting portion 331 of the switching portion 330.

For example, a blade surface 331a of the cutting portion 331 of the switching portion 330 can be configured to include a trepanned blade surface. In addition, in a case where the blade surface 331a is configured to include the trepanned blade surface, for example, the blade surface 21a of the cutting edge 21 of the rotary body 20 can be configured to include the blade surface having a saw-tooth shape. In a case where the shape of the respective blade surfaces 21a and 331a is configured in this way, the treatment for cutting off the stenosed site S having a soft tissue by using the blade surface 331a included in the switching portion 330 and the treatment for finely crushing the calcified lesion by using the blade surface 21a included in the rotary body 20 can be realized using a single medical device. Furthermore, the blade surface 331a of the switching portion 330 which first applies the cutting force to the stenosed site S is configured to include the trepanned blade surface. Accordingly, after the blade surface 331a forms a cutout portion in the stenosed site S, the blade surface 21a configured to have the saw-tooth shape can enter the cutout portion. The blade surface 21a easily enters the inside of the stenosed site S. Accordingly, the stenosed site S can be more finely crushed by the blade surface 21a, and the therapeutic effect can be improved. Furthermore, the blade surface 331a of the switching portion 330 located on the distal side beyond the rotary body 20 is configured to include the smooth blade surface such as the trepanned blade surface. Accordingly, the safety for the vascular wall is improved.

The shape of the blade surface 21a included in the rotary body 20 and the shape of the blade surface 331a included in the switching portion 330 are not limited to the illustrated examples, and can be appropriately changed. For example, both the blade surfaces 21a and 331a can be configured to include the blade surface having the saw-tooth shape or the trepanned blade surface. Alternatively, the blade surface 331a included in the switching portion 330 can be configured to include the blade surface having the saw-tooth shape, and the blade surface 21a included in the rotary body 20 can be configured to include the trepanned blade surface.

Next, a medical device according to Modification Example 5 of the first exemplary embodiment will be described.

Figure 10:
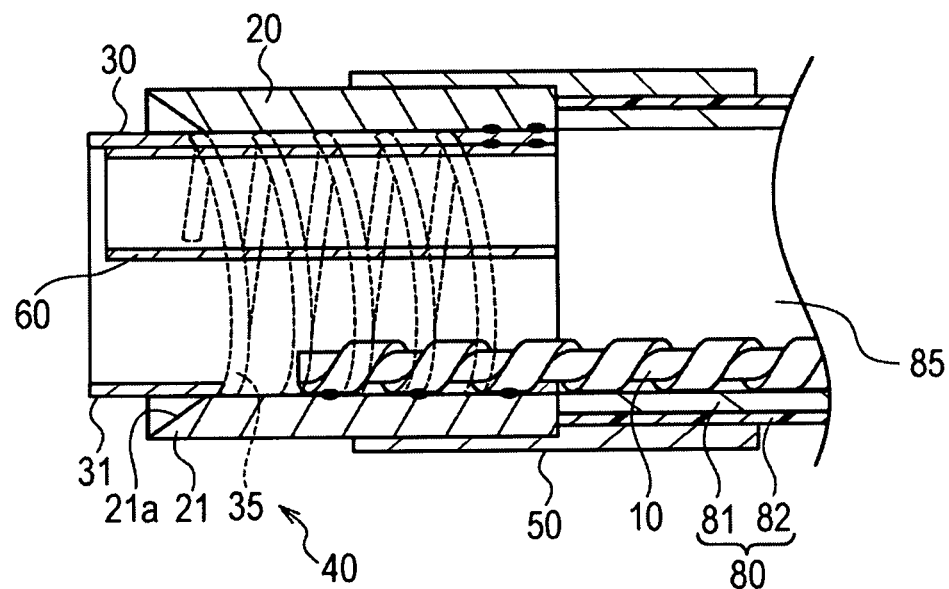
FIG. 10 is a cross-sectional view illustrating a medical device according to Modification Example 5 of the first exemplary embodiment.

As illustrated in FIG. 10, this modification example employs an arrangement in which the position of the distal end of the cutting assistance portion 60 is located on the proximal side beyond the switching portion 30, in a state where the external force is not applied to the switching portion 30. Even in this arrangement, the pushing force for pushing the switching portion 30 against the stenosed site S is adjusted. In this manner, the cutting assistance portion 60 can protrude from the distal end of the switching portion 30, and the cutting can be performed using the cutting assistance portion 60. In addition, in a state where the external force is not applied to the switching portion 30, the switching portion 30 functions as the protector, and the cutting assistance portion 60 can be prevented from inadvertently coming into contact with the biological tissue. Accordingly, the safety when in use is further improved. For example, even in a case where the cutting assistance portion 60 includes the blade surface having the relatively strong cutting force and the saw-tooth shape, non-corrugated blade, the safety when in use can be maintained extremely high. Therefore, the structure or the shape of the cutting assistance portion 60 can be more freely designed in a wider range, and various functions can be provided for the cutting assistance portion 60.

In a state where the external force is not applied to the switching portion 30, for example, the distal end of the cutting assistance portion 60 may be disposed on the distal side beyond the distal end of the cutting edge 21, or may be disposed at a position which is the same as that of the distal end of the cutting edge 21.

Next, a medical device according to Modification Example 6 of the first exemplary embodiment will be described.

Figure 11:
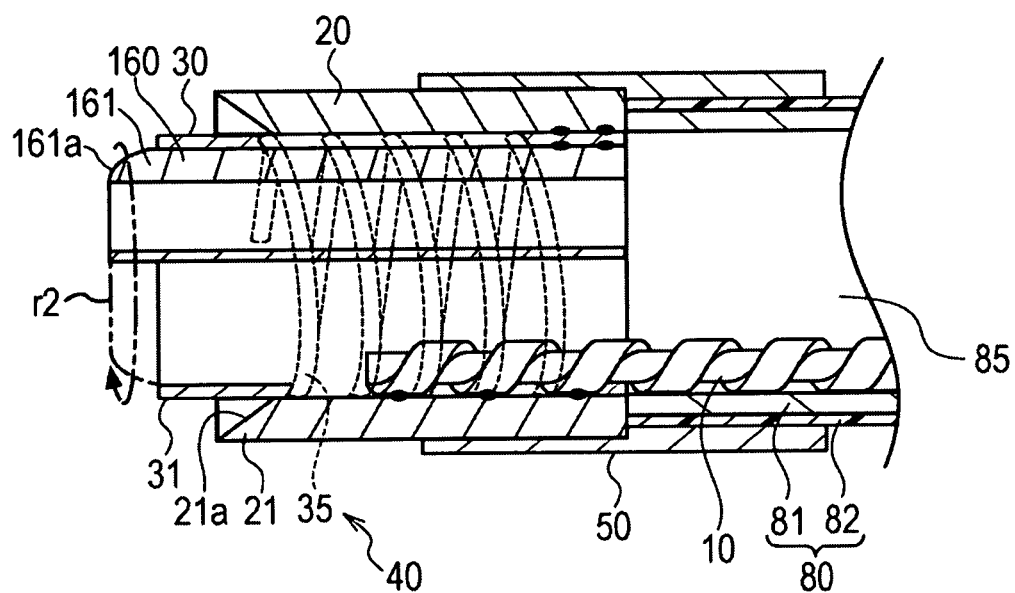
FIG. 11 is a cross-sectional view illustrating a medical device according to Modification Example 6 of the first exemplary embodiment.

As illustrated in FIG. 11, in this modification example, a chamfered portion 161a subjected to chamfering in an R-shape is disposed in a distal end 161 of the cutting assistance portion 160. The R-shape is an atraumatic configuration defining a dome configuration. The chamfered portion 161a is disposed in the cutting assistance portion 160. Accordingly, when the cutting is performed by rotating the rotary body 20, an orbit r2 drawn by the cutting assistance portion 160 forms a convex shape (dome shape) curved from the distal side toward the proximal side. Even if the cutting assistance portion 60 comes into contact with the vascular wall during the treatment, it is possible to prevent a force from being applied to and scratching the vascular wall. Accordingly, the safety when in use can be further improved.

A curvature of the chamfered portion 161a is not particularly limited, and can be appropriately changed.

Next, a medical device 100 according to Modification Example 7 of the first exemplary embodiment will be described.

Figure 12:
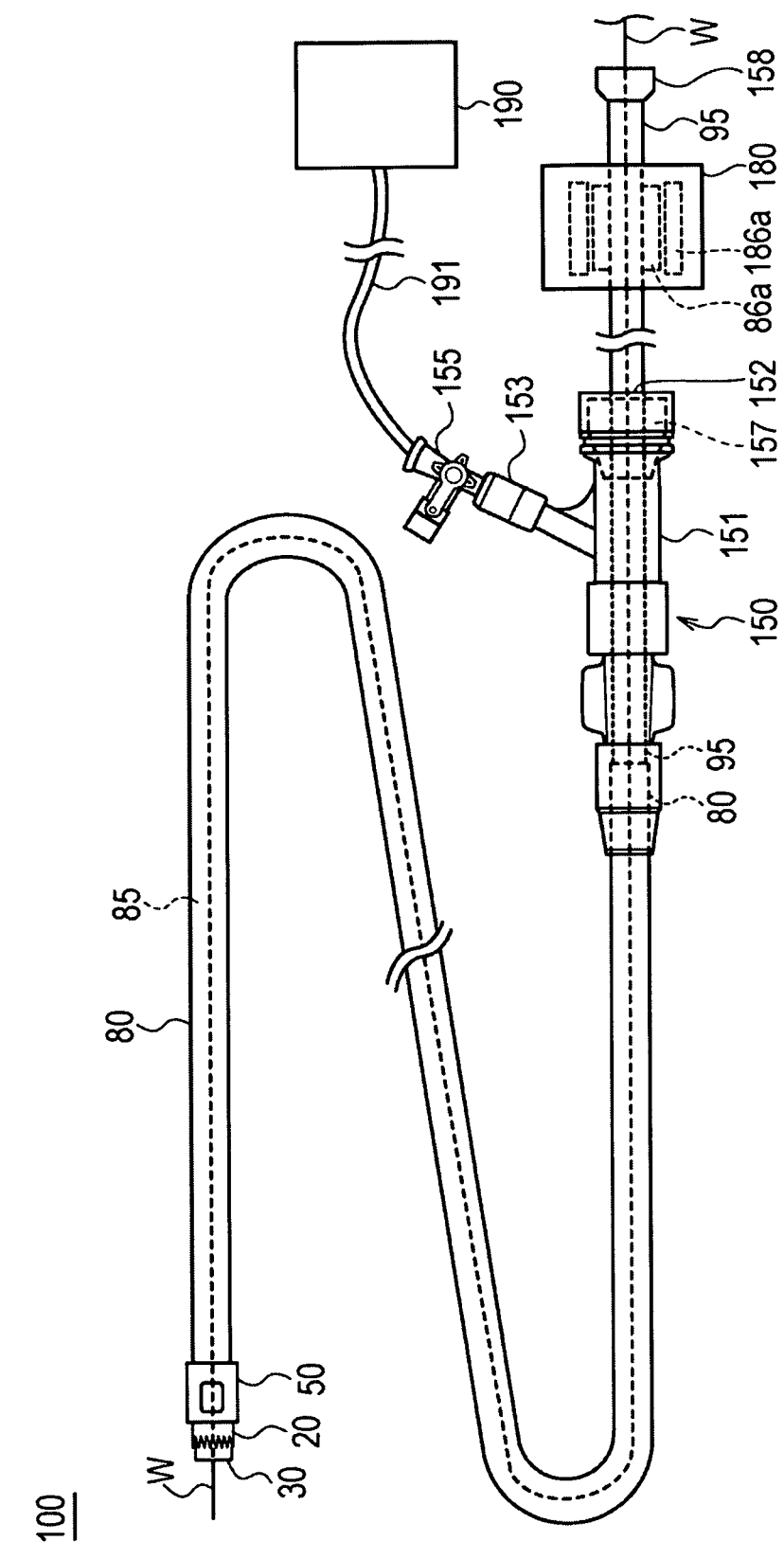
FIG. 12 is a plan view illustrating a medical device according to Modification Example 7 of the first exemplary embodiment.
Figure 13A:
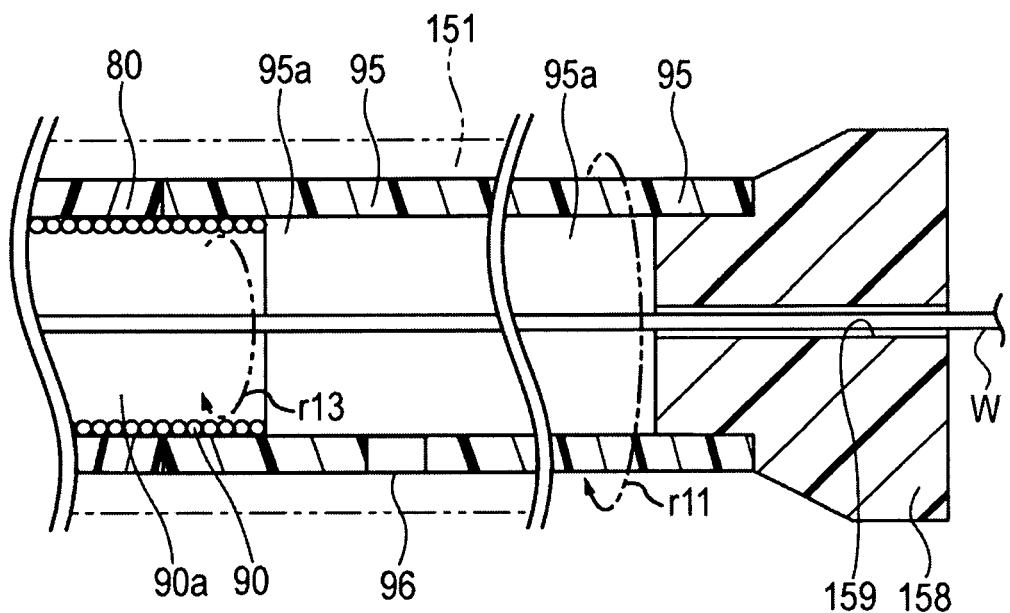
FIG. 13A is an enlarged cross-sectional view illustrating a configuration of a proximal portion of the medical device according to Modification Example 7.
Figure 13B:
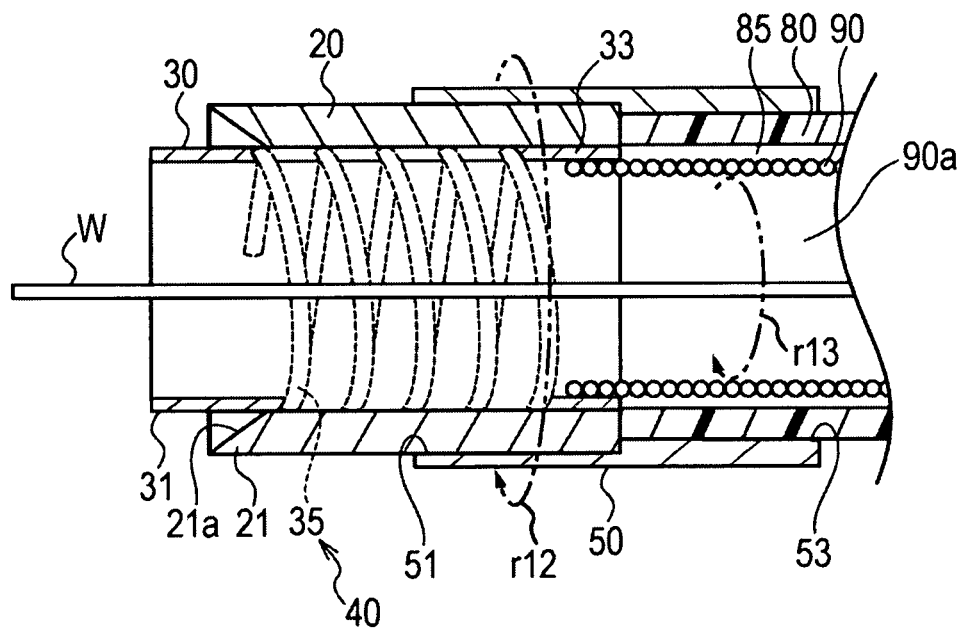
FIG. 13B is an enlarged cross-sectional view illustrating a configuration of a distal portion of the medical device according to Modification Example 7.

In this modification example, a configuration of each portion of the medical device 100 is modified so that the treatment using a guide wire W can be more smoothly performed. In the medical device 1 described above, an example has been described in which the drive shaft 10 is used as the elongated member for transmitting the rotational force to the rotary body 20. In the medical device 100 according to this modification example, a coil 90 is used as the elongated member for transmitting the rotational force to the rotary body 20. FIG. 12 is a plan view illustrating an overall configuration of the medical device 100 according to this modification example. FIG. 13A is an enlarged cross-sectional view illustrating the periphery of the proximal portion. FIG. 13B is an enlarged cross-sectional view illustrating the periphery of the distal portion.

As illustrated in FIG. 13B, the coil 90 is inserted into the lumen 85 of the tube 80. The rotary body 20 is attached to the distal end of the coil 90. In addition, the rotation receiving portion 50 is attached to the distal end of the tube 80.

As illustrated in FIG. 13A, a relay tube 95 is attached to the proximal end of the tube 80. The proximal end of the coil 90 is attached to the inner surface of the distal end of the relay tube 95.

As illustrated in FIG. 13A, the hub 151 is attached so as to surround the outer periphery of the relay tube 95. As illustrated in FIG. 12, the proximal portion of the relay tube 95 is pulled out from the hub 151 by being inserted into the proximal end port 152 of the hub 151. In addition, the relay tube 95 is inserted into the valve body 157 disposed inside the hub 151.

As illustrated in FIG. 13A, an opening portion 96 is disposed in the relay tube 95. A lumen 95a of the relay tube 95 communicates with the interior of the connector portion 153 disposed in the hub 151 via the opening portion 96. The debris D generated during the treatment using the medical device 100 can be discharged outward of the relay tube 95 through the lumen 95a and the opening portion 96 of the relay tube 95.

As illustrated in FIG. 13B, the coil 90 is surrounded by the tube 80. The tube 80 prevents the aspirated fluid and the debris D from leaking out through a gap of the coil 90. For example, the tube 80 can be configured to include a resin-made single layer tube formed of a known resin material.

The relay tube 95 is configured to be rotatable by the rotational drive force transmitted from the external drive apparatus 180. As illustrated in FIG. 12, the external drive apparatus 180 is provided with a second movement mechanism 186a which applies the rotational drive force to the relay tube 95 in cooperation with a first movement mechanism 86a disposed in the relay tube 95. For example, the first movement mechanism 86a can be configured to include a driven gear. For example, the second movement mechanism 186a can be configured to include a driving gear meshing with the driven gear. For example, the external drive apparatus 180 includes a known drive unit such as an electric motor including the drive shaft.

If a power source is turned on for the external drive apparatus 180 and the drive shaft is rotated by supplying a drive current, the driving gear (second movement mechanism) 186a is rotated, and the driven gear (first movement mechanism) 86a is rotated in response to the rotation of the driving gear 186a. If the driven gear 86a is rotated, the relay tube 95 is rotated in response to the rotation (an arrow r11 in FIG. 13A indicates the rotation). If the relay tube 95 is rotated, the coil 90 attached to the relay tube 95 is rotated (an arrow r13 in FIGS. 13A and 13B indicates the rotation). Then, if the coil 90 is rotated, the rotary body 20 disposed in the distal end of the coil 90 is rotated (an arrow r12 in FIG. 13B indicates the rotation).

As illustrated in FIG. 13A, a valve body 158 is disposed in the proximal end of the relay tube 95. The valve body 158 is provided with an insertion hole 159 into which the guide wire W is inserted. The guide wire W is inserted into the lumen 95a of the relay tube 95 by inserting the valve body 158. In addition, as illustrated in FIG. 136, the guide wire W is inserted into the lumen 95a of the relay tube 95, and the distal portion is guided into the lumen 90a of the coil 90 disposed in the distal end of the relay tube 95, the rotary body 20, and the switching portion 30. The guide wire W is pulled out from the distal opening portion of the switching portion 30, and the distal portion is guided to the distal side of the rotary body 20. The guide wire W can be easily inserted from the proximal end to the distal end of the relay tube 95. Accordingly, when the treatment is performed using the medical device 100, the guide wire W can be smoothly operated.

In this modification example, in order to smoothly and easily insert the guide wire W into the rotary body 20 and the switching portion 30, the cutting assistance portion 60 is not disposed in the rotary body 20.

A material or a structure of the coil 90 and the relay tube 95 is not particularly limited, as long as both of these can be configured so that the rotary body 20 can be rotated in conjunction with the rotation. In addition, a fixing method or a fixing position between the coil 90 and the tube 80, a fixing method or a fixing position between the relay tube 95 and the tube 80, and a fixing method or a fixing position between the coil 90 and the relay tube 95 are not particularly limited, as long as the rotational drive force can be transmitted to the rotary body 20.

In the above-described exemplary first embodiment and the respective modification examples, the tubular rotary body having the cutting edge formed on the distal surface has been described as an example. However, a configuration of the rotary body is not particularly limited, as long as the cutting can be performed using the cutting edge. For example, the cutting edge may be formed on the side surface of the rotary body instead of the front surface of the rotary body. In addition, a shape or a material of additional members such as the rotation receiving portion and the cutting assistance portion can be appropriately modified in accordance with product specifications of the medical device, and the shape or the material is not limited to the above-described configuration.

Second Embodiment

Next, a medical device 2 according to a second exemplary embodiment will be described. In describing the second embodiment, description will be appropriately omitted with regard to members which can be configured similar to the medical device 1 and the medical device 100 according to the first exemplary embodiment described above. In addition, structures which are not specifically described in the second exemplary embodiment can be configured similar to the first embodiment.

Figure 14:
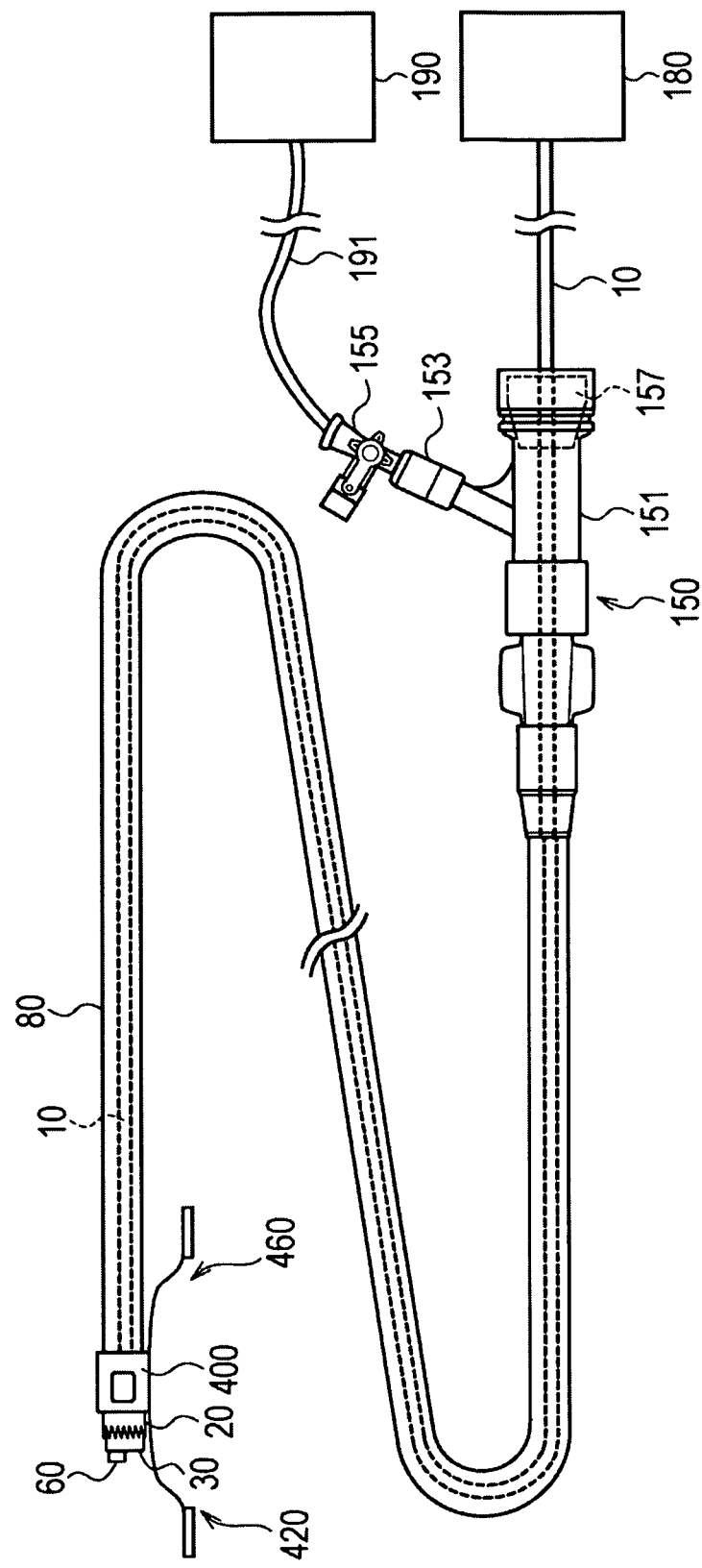
FIG. 14 is a plan view of a medical device according to a second exemplary embodiment.

Referring to FIG. 14, the medical device 2 according to the second exemplary embodiment is different from the above-described medical device 1 in a structure on the distal side of the tube 80. Specifically, the medical device 2 has a distal member 400 for adjusting a contact position where the rotary body 20 is brought into contact with the stenosed site S when the rotary body 20 is used so as to treat the stenosed site S (refer to FIG. 18B).

As illustrated in FIG. 14, in brief, the medical device 2 has the rotatable drive shaft 10, the rotary body 20 including the cutting edge 21 and rotated in conjunction with the rotation of the drive shaft 10, the protector (switching portion) 30, the cutting assistance portion 60, and the distal member 400 disposed in the rotary body 20.

Figure 15A:
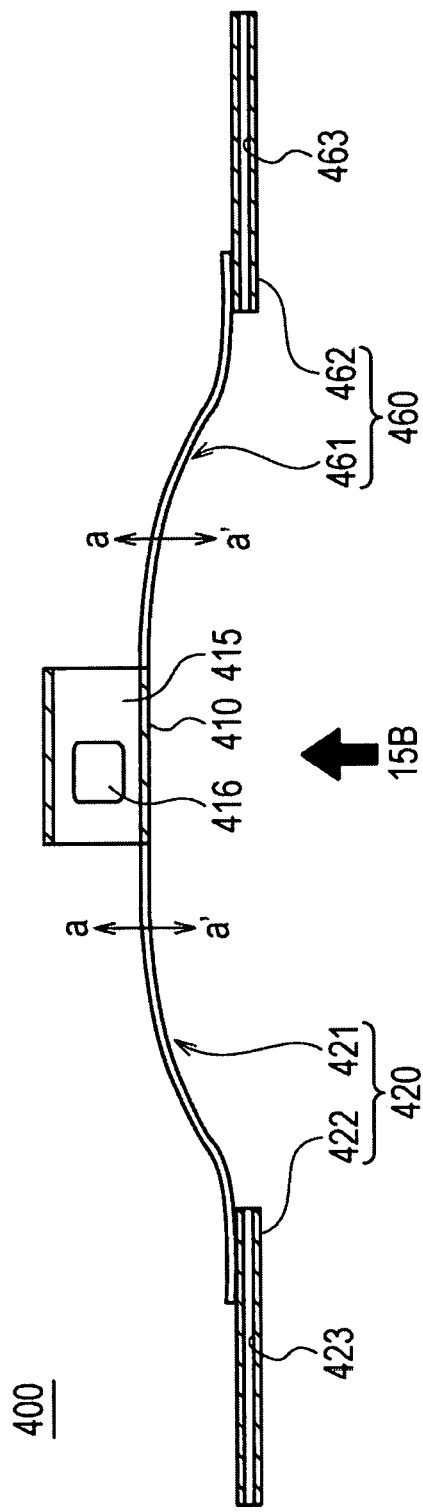
FIG. 15A is a partial cross-sectional view of a distal member included in the medical device according to the second exemplary embodiment.

As illustrated in FIGS. 15A and 15B, the distal member 400 has a hollow main body portion 410 including a lumen 415 and a side hole 416 open on the side surface, and a support portion 420 that extends to the distal side beyond the distal end of the rotary body 20, and that is configured to be capable of supporting the rotary body 20 with respect to the biological lumen such as the blood vessel H.

Figure 16A:
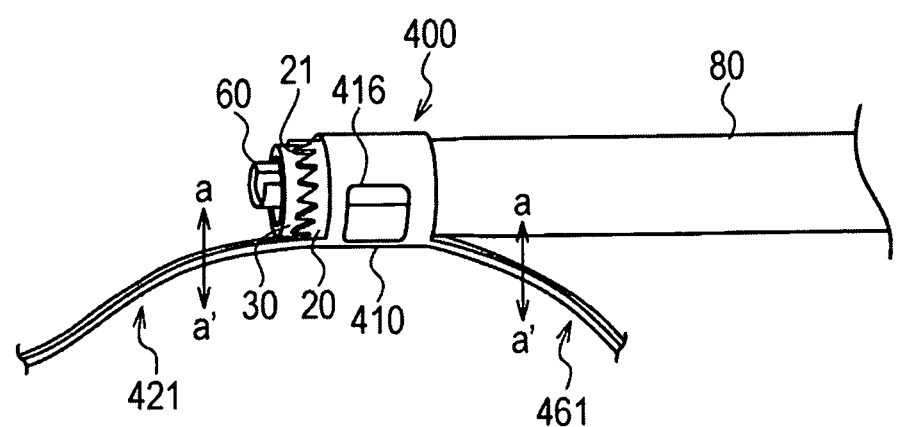
FIG. 16A is a perspective view illustrating a distal side of the medical device according to the second exemplary embodiment.

The rotary body 20 can be inserted into and disposed in the main body portion 410 of the distal member 400. The main body portion 410 holds the rotary body 20 in the lumen 415. The main body portion 410 is provided with a function to serve as the rotation receiving portion which prevents the rotary shaft of the rotary body 20 from being deviated, when the rotary body 20 is rotated. As illustrated in FIG. 16A, the distal member 400 is mounted on the outer surface of the rotary body 20.

The support portion 420 of the distal member 400 is disposed so as to extend to the distal side beyond the distal end of the rotary body 20 in a state where the rotary body 20 is inserted into the main body portion 410 (refer to FIG. 14). The support portion 420 is configured so that the distance from the rotary body 20 is variable in a first direction (the direction of an arrow a-a' in FIG. 15A) which intersects the extending direction of the rotary body 20.

In the second exemplary embodiment, the first direction is set to a vertical direction (also referred to as a "height direction") orthogonal to the extending direction (axial direction) of the distal member 400. However, the first direction is not particularly limited, as long as the first direction is a direction in which the rotary body 20 is moved close to the stenosed site S serving as the cutting target in the medical procedure using the medical device 2. The first direction is not limited to only the vertical direction.

The support portion 420 has an elastically deformable first site 421 that extends gradually away from the rotary body 20 in the first direction, and a second site 422 that extends to the distal side beyond the first site 421 and that has a guide wire insertion portion (lumen) 423 into which the guide wire W can be inserted.

In a state where the external force is not applied, the first site 421 of the support portion 420 has a shape protruding outward beyond the rotary body 20 in a second direction (direction of an arrow b-b' in FIG. 15B) intersecting each of the first direction and the extending direction of the rotary body 20.

In the second exemplary embodiment, the second direction is set to a horizontal direction (also referred to as a "width direction") orthogonal to the first direction. However, the second direction is not particularly limited, as long as the rotary body 20 can align with a predetermined position in the medical procedure using the medical device 2. For example, the second direction can be appropriately changed in conjunction with the change in the first direction.

As illustrated in FIG. 15B, the first site 421 has a shape spreading in a direction symmetrical to a rotary shaft R1 of the rotary body 20. In addition, the first site 421 is configured to include a first arm portion 421a and a second arm portion 421b.

The first arm portion 421a and the second arm portion 421b have a substantially symmetrical shape with reference to the rotary shaft R1. The proximal end of the first arm portion 421a and the proximal end of the second arm portion 421b are connected to the main body portion 410, and the distal end of the first arm portion 421a and the distal end of the second arm portion 421b are connected to the second site 422. An annular space is defined between the respective arm portions 421a and 421b. As illustrated in FIG. 15A, the respective arm portions 421a and 421b have a convex shape which is gently curved from the main body portion 410 toward the distal side along the first direction. The distal side connected to the second site 422 is farthest away from the main body portion 410.

As illustrated in FIGS. 15A and 15B, the distal member 400 further has an auxiliary support portion 460 that extends to the proximal side beyond the proximal end of the rotary body 20 and that is configured to be capable of supporting the rotary body 20 with respect to the blood vessel H. The auxiliary support portion 460 has a shape substantially symmetrical to the support portion 420 with reference to the center position of the main body portion 410. Similar to the support portion 420, the auxiliary support portion 460 is configured so that the distance from the rotary body 20 is variable in the first direction (direction of the arrow a-a' in FIG. 15A) which intersects the extending direction of the rotary body 20.

The auxiliary support portion 460 has an elastically deformable first auxiliary site 461 that extends gradually away from the rotary body 20 in the first direction, and a second auxiliary site 462 that extends to the proximal side beyond the first auxiliary site 461 and that has a guide wire insertion portion (lumen) 463 into which a guide wire W can be inserted.

In a state where the external force is not applied, the first auxiliary site 461 of the auxiliary support portion 460 has a shape protruding outward beyond the rotary body 20 in the second direction (direction of the arrow b-b' in FIG. 15B).

The first auxiliary site 461 has a shape spreading in the direction symmetrical to the rotary shaft R1 of the rotary body 20. The first auxiliary site 461 is configured to include a first arm portion 461a and a second arm portion 461b. The first arm portion 461a and the second arm portion 461b are configured to have substantially the same shape as the respective arm portions 421a and 421b included in the support portion 420. Accordingly, description of the shape will be omitted.

The main body portion 410, the support portion 420, and the auxiliary support portion 460 of the distal member 400 can be integrally configured to include a known metal material or resin material, for example. In the second exemplary embodiment, the above-described members are integrally configured to include metal provided with biocompatibility. In addition, each outer surface of the main body portion 410, the support portion 420, and the auxiliary support portion 460 is coated with a resin-made coating member (for example, a known heat-shrinkable tube). The above-described members can be integrally interlocked with each other by thermally shrinking the coating member.

The first site 421 of the support portion 420 and the first auxiliary site 461 of the auxiliary support portion 460 can be configured to include a flat plate-shaped member, for example. In addition, the second site 422 of the support portion 420 and the second auxiliary site 462 of the auxiliary support portion 460 can be configured to internally include a hollow tubular member, for example.

As illustrated in FIG. 16A, the distal member 400 is mounted on the outer surface of the rotary body 20, when the treatment is performed using the medical device 2. The support portion 420 (first site 421) and the auxiliary support portion 460 (first auxiliary site 461) of the distal member 400 generate tension for raising the rotary body 20 upward (in a direction of an arrow a in the drawing). A position for mounting the distal member 400 on the rotary body 20 can be appropriately set to a position at which the cutting edge 21 of the rotary body 20 is not covered by the distal end of the distal member 400. A distance (height) for raising the rotary body 20 can be set within 7 mm, for example, in a case where the medical device 2 is applied to the treatment for the blood vessel H.

In addition, the distal member 400 is externally mounted on the rotary body 20. Accordingly, the support portion 420 or the auxiliary support portion 460 included in the distal member 400 does not need to be accommodated in or inserted into the rotary body 20. Therefore, the rotary body 20 itself can be avoided from increasing in diameter. Accordingly, it is possible to prevent the rotary body 20 from being unsatisfactorily delivered into the blood vessel H due to the increased diameter of the rotary body 20, and it is possible to prevent the rotary body 20 from being unsatisfactorily inserted into the stenosed site S.

Figure 16B:
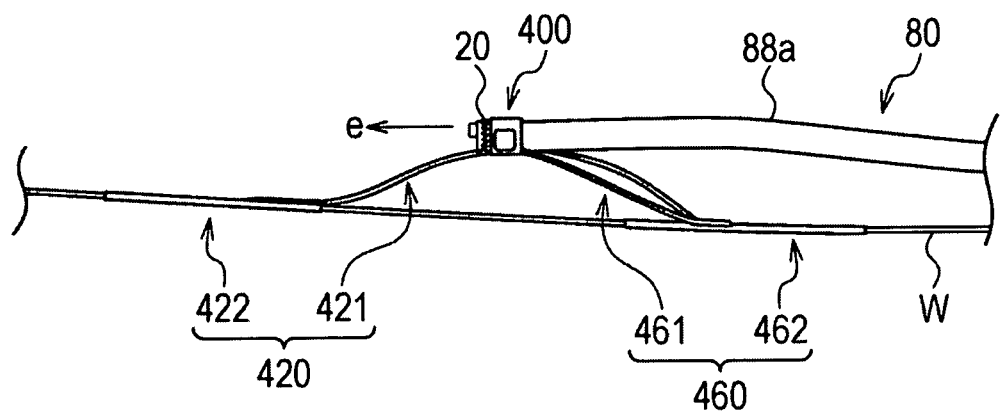
FIG. 16B is a side view for describing a structure of an elongated member included in the medical device according to the second exemplary embodiment.

As illustrated in FIG. 16B, a curved shape is added to the distal portion 88a of the tube 80. The curved shape is added so as to prevent an orientation of the distal surface of the rotary body 20 from being inclined upward or downward. For example, when the treatment is performed using the rotary body 20, if the guide wire W is inserted into the second site 422 and the second auxiliary site 462, due to the elasticity of the guide wire W, the first site 421 of the support portion 420 and the first auxiliary site 461 of the auxiliary support portion 460 may be curved so as to follow the curve of the guide wire W, in some cases. If these are curved in this way, the orientation of the distal surface of the rotary body 20 which is indicated by an arrow e is inclined upward or downward, thereby causing a possibility that the orientation of the cutting edge 21 may be directed in an unintended direction. As illustrated, a predetermined curved shape is added to the distal portion 88a of the tube 80 so as to be capable of maintaining a state where the orientation of the rotary body 20 faces the front surface. In this manner, it is possible to adjust the orientation of the rotary body 20 so as to face the front surface side when the cutting is performed.

Figure 17A:
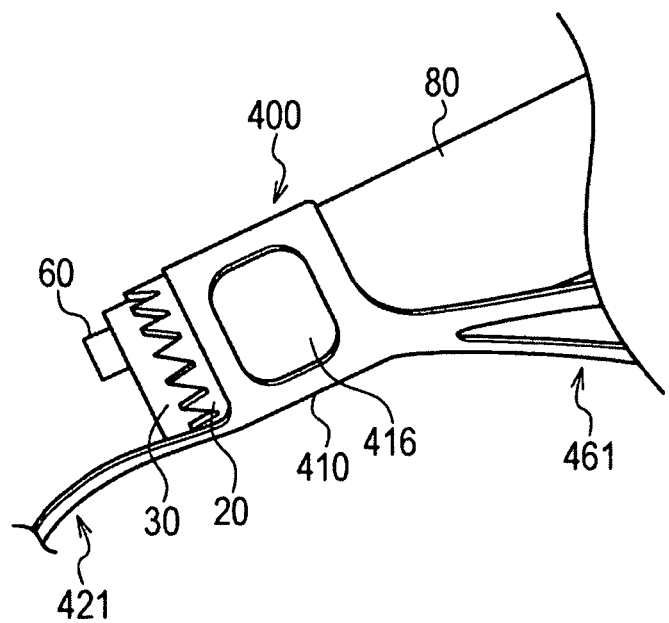
FIG. 17A is a perspective view for describing an operation of a side hole belonging to the distal member included in the medical device according to the second exemplary embodiment.
Figure 17B:
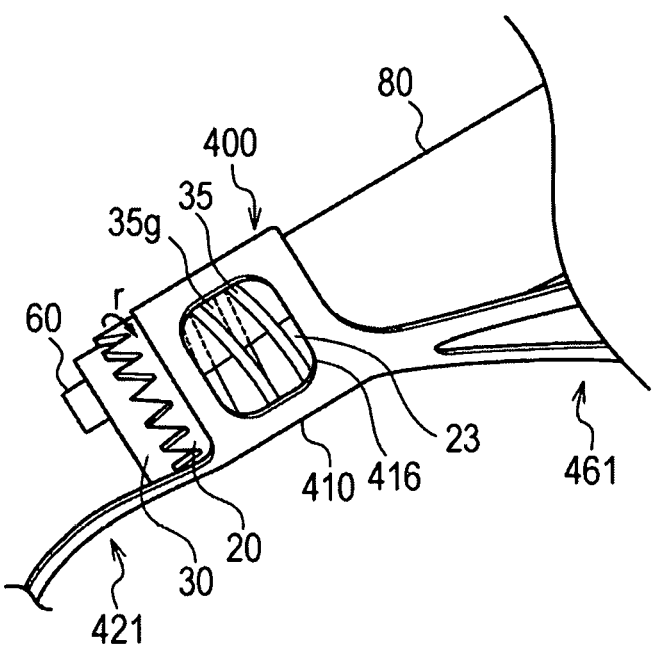
FIG. 17B is a perspective view for describing an operation of the side hole belonging to the distal member included in the medical device according to the second exemplary embodiment.

When the treatment is performed using the rotary body 20, a state illustrated in FIG. 17A is switched to a state illustrated in FIG. 17B in accordance with the rotation of the rotary body 20. The state illustrated in FIG. 17A means a state where the debris D is prevented from flowing from the side surface of the rotary body 20, and the state illustrated in FIG. 17B means a state where the debris D can flow from the side surface of the rotary body 20. Since the rotary body 20 is rotated, if the side hole 23 disposed on the side surface of the rotary body 20 and the side hole 416 disposed on the side surface of the distal member 400 are disposed so as to overlap each other, the inner side and the outer side of the rotary body 20 are brought into a communicating state. Accordingly, the debris D flows into the rotary body 20 and into the holding portion 40 (stretchable and deformable portion 35) via the side hole 23. The debris D flows into the tube 80, and is collected on the proximal side of the tube 80. The debris D can be collected via the side hole 23. Accordingly, similar to the above-described embodiment, it is possible to improve efficiency in collecting the debris D.

Next, a treatment method using the medical device 2 will be described with reference to FIGS. 18A to 18C. Herein, a method of cutting the stenosed site S formed in the blood vessel H will be described as an example.

Figure 18A:
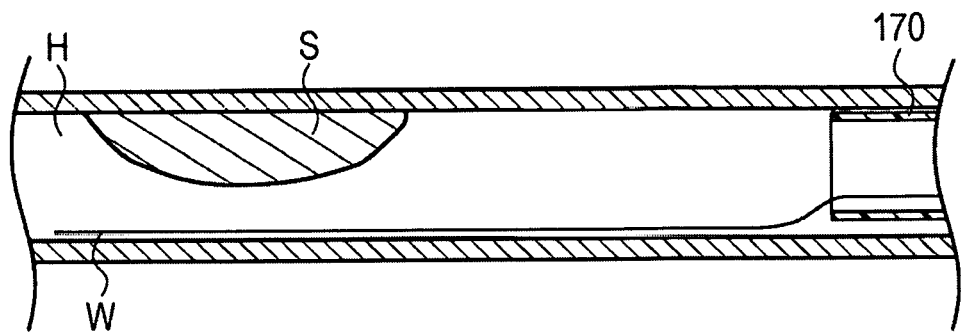
FIG. 18A is a cross-sectional view schematically illustrating a treatment example using medical device according to the second exemplary embodiment.

First, as illustrated in FIG. 18A, the guiding sheath 170 is introduced to the vicinity of the stenosed site S. The guiding sheath 170 can be delivered to the vicinity of the stenosed site S along the previously introduced guide wire W.

Next, the medical device 2 is delivered to the vicinity of the stenosed site S along with the guide wire W. In this case, the guide wire W is inserted into the second site 422 of the support portion 420 and the second auxiliary site 462 of the auxiliary support portion 460. In this manner, the distal member 400 can be smoothly moved to a predetermined position. In a state where the distal member 400 is accommodated inside the guiding sheath 170, the distal member 400 is pushed against the inner wall of the guiding sheath 170, and is shrunk in the height direction (direction of the arrow a' in FIG. 15) and the width direction (direction of the arrow b' in FIG. 15).

Figure 18B:
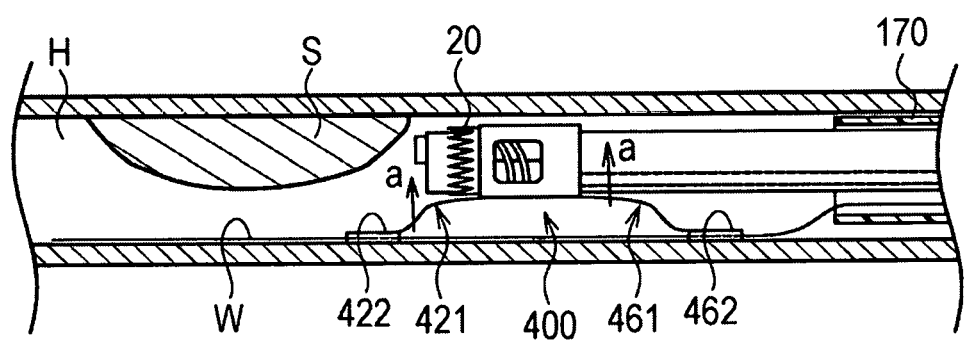
FIG. 18B is a cross-sectional view schematically illustrating a treatment example using medical device according to the second exemplary embodiment.

As illustrated in FIG. 18B, if the distal member 400 protrudes outward of the guiding sheath 170 via the distal opening portion of the guiding sheath 170, the first site 421 of the support portion 420 is deformed so as to spread in the height direction and the width direction, until the first site 421 of the support portion 420 is attached to the inner wall of the blood vessel H. Similarly, the first auxiliary site 461 of the auxiliary support portion 460 is deformed so as to spread in the height direction and the width direction, until the first auxiliary site 461 of the auxiliary support portion 460 is attached to the inner wall of the blood vessel H.

The rotary body 20 having the distal member 400 attached thereto is raised in the height direction. In this manner, the rotary body 20 is disposed at a position facing the stenosed site S formed on the inner wall of the blood vessel H. In addition, the first site 421 and the first auxiliary site 461 which spread in the width direction cause the rotary body 20 to be disposed at a position where the rotary shaft R1 overlaps the respective guide wire insertion portions 423 and 463 (refer to FIG. 15B). In this manner, the rotary shaft R1 passing through the center of the distal member 400 is disposed substantially parallel to the delivery of the guide wire W. If the rotary body 20 is moved toward the stenosed site S in this state, the rotary body 20 moves parallel to the delivery of the guide wire W, and is pushed against the stenosed site S, in a state where the cutting edge 21 located in the distal end of the rotary body 20 faces the stenosed site S.

As described above, the rotary body 20 comes into contact with the stenosed site S serving as the cutting target after the position is appropriately adjusted in the height direction and the width direction (the height direction and the width direction on the axially orthogonal cross-section) of the blood vessel H. Accordingly, the cutting force generated by the cutting edge 21 can satisfactorily act on the stenosed site S, and the stenosed site S can be efficiently cut.

In addition, the first site 421 of the support portion 420 and the first auxiliary site 461 of the auxiliary support portion 460 are elastically deformed in response to the inner diameter of the blood vessel H. Accordingly, in a state where the external force is not applied, even in a case where the blood vessel H having a smaller inner diameter dimension than the first site 421 and the first auxiliary site 461 is the treatment target, the diameter of the whole distal member 400 is reduced, and the distal member 400 is moved inside the blood vessel H. Therefore, the medical device 2 can be satisfactorily delivered into the living body.

Figure 18C:
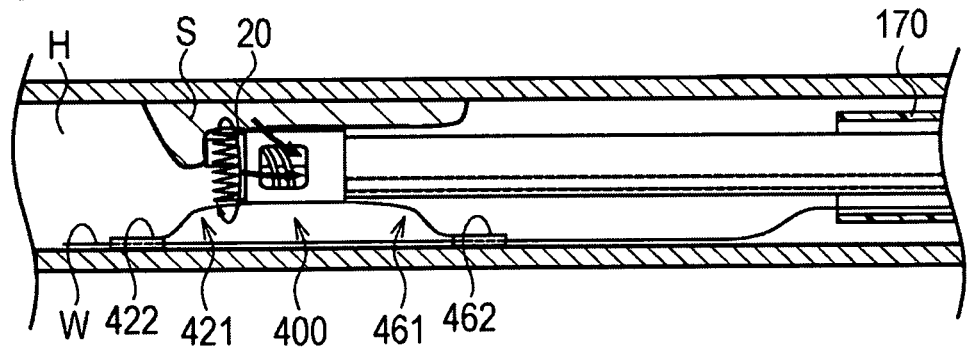
FIG. 18C is a cross-sectional view schematically illustrating a treatment example using medical device according to the second exemplary embodiment.

Next, as illustrated in FIG. 18C, the medical device 2 is moved to the distal side so that the cutting edge 21 of the rotary body 20 is pushed against the stenosed site S, thereby cutting the stenosed site S. When the cutting edge 21 is rotated so as to cut off the stenosed substance of the stenosed site S, for example, the aspiration device 190 can be operated so as to aspirate the scraped debris D into the rotary body 20.

After the cutting treatment is completely performed on the stenosed site S, the medical device 2 is appropriately removed outward of the living body. It is also possible to subsequently perform the cutting treatment on the other stenosed site S.

As described above, the medical device 2 according to the second exemplary embodiment has the rotatable drive shaft 10, the rotary body 20 that includes the cutting edge 21 for applying the cutting force to the stenosed site S, and that is disposed on the distal side of the drive shaft 10 so as to be rotated in conjunction with the rotation of the drive shaft 10, and the distal member 400 disposed in the rotary body 20. The distal member 400 has the support portion 420 that extends to the distal side beyond the distal end of the rotary body 20, and that is configured to be capable of supporting the rotary body 20 with respect to the blood vessel H. The support portion 420 is configured so that the distance from the rotary body 20 is variable in the first direction (height direction) in which the rotary body 20 is moved close to the stenosed site S.

According to the medical device 2 configured as described above, the rotary body 20 is supported by the support portion 420 so as to align with the stenosed site S inside the blood vessel H. In a state where the rotary body 20 aligns with the stenosed site S, the cutting edge 21 comes into contact with the stenosed site S. Accordingly, the cutting force can be satisfactorily applied to the stenosed site S. In this manner, the stenosed site S can be efficiently cut, and further, the cutting edge 21 can be preferably prevented from coming into contact with the biological tissue other than the stenosed site S.

In addition, the support portion 420 has the elastically deformable first site 421 that extends gradually away from the rotary body 20 in the first direction, and the second site 422 that extends to the distal side beyond the first site 421, and that includes the guide wire insertion portion 423 into which the guide wire W can be inserted. Therefore, since the elastic deformation of the first site 421 is used, the rotary body 20 can easily align with the stenosed site S. Furthermore, the guide wire W is inserted into the guide wire insertion portion 423. In this manner, the distal member 400 of the medical device 2 can be delivered to a predetermined position inside the living body. Accordingly, excellent operability is achieved.

In a state where the external force is not applied, the first site 421 has a shape protruding outward beyond the rotary body 20 in the second direction which intersects each of the first direction and the extending direction of the rotary body 20. Therefore, the first site 421 is likely to be attached to the inner wall of the blood vessel H. This attachment allows the distal member 400 to be supported on the inner wall of the blood vessel H. The distal member 400 is supported on the inner wall of the blood vessel H. Accordingly, it is possible to prevent the rotary shaft of the rotary body 20 from being deviated when the stenosed site S is cut. Therefore, the stenosed site S can be efficiently cut.

In addition, the first site 421 has the shape spreading in the direction symmetrical to the rotary shaft R1 of the rotary body 20. Accordingly, the center position of the distal member 400 can align with the rotary shaft R1 of the rotary body 20. Furthermore, the center position of the distal member 400 can align with the center position in the width direction of the blood vessel H. Therefore, the stenosed site S can be more efficiently cut.

The distal member 400 further has the auxiliary support portion 460 that extends to the proximal side beyond the proximal end of the rotary body 20, and that is configured to be capable of supporting the rotary body 20 with respect to the blood vessel H. In this manner, the distal member 400 can be raised on the distal side and the proximal side of the distal member 400. Accordingly, the distal member 400 can be more reliably raised, and it is possible to prevent a gap in the height direction from being generated between the distal side and the proximal side of the distal member 400 when the distal member 400 is raised. Therefore, the rotary body 20 can properly align with the stenosed site S.

The auxiliary support portion 460 has the elastically deformable first auxiliary site 461 that extends gradually away from the rotary body 20 in the first direction, and the second auxiliary site 462 that extends to the proximal side beyond the first auxiliary site 461, and that includes the guide wire insertion portion 463 into which the guide wire W can be inserted. Therefore, the rotary body 20 can be raised to a proper position by the first site 421 of the support portion 420 and the first auxiliary site 461 of the auxiliary support portion 460. Moreover, the distal member 400 can be smoothly moved to a predetermined position by the guide wire W inserted into the second site 422 of the support portion 420 and the second auxiliary site 462 of the auxiliary support portion 460.

The treatment method according to the second exemplary embodiment has the cutting step of bringing the rotary body 20 including the cutting edge 21 for applying the cutting force to the stenosed site S inside the blood vessel H into a supported state in the first direction (height direction) in which the rotary body 20 is moved close to the stenosed site S, and performing the cutting by bringing the cutting edge 21 into contact with the stenosed site S while rotating the rotary body 20.

According to the treatment method having the above-described step, the rotary body 20 is supported, and the position of the rotary body 20 is adjusted with respect to the stenosed site S inside the blood vessel H. Thereafter, the stenosed site S is cut by the rotary body 20. In this manner, the cutting force can satisfactorily act on the stenosed site S. Furthermore, the cutting edge 21 can be preferably prevented from coming into contact with the biological tissue other than the stenosed site S.

In addition, the cutting step can be performed in a state where the rotary body 20 is supported in the second direction (width direction) which intersects each of the first direction and the extending direction of the rotary body 20. Accordingly, the distal member 400 can be supported inside the blood vessel H in a more stable state. The rotary shaft of the rotary body 20 can be prevented from being deviated when the stenosed site S is cut. In this manner, the stenosed site S can be efficiently cut.

In addition, the cutting step can be performed in a state where the rotary body 20 is supported by the support portion 420 extending to the distal side of the rotary body 20 and the auxiliary support portion 460 extending to the proximal side of the rotary body 20. In this manner, the distal member 400 can be more reliably raised, and it is possible to prevent a gap in the height direction from being generated between the distal side and the proximal side of the distal member 400 when the distal member 400 is raised. Therefore, the rotary body 20 can properly align with the stenosed site S.

The treatment method also may have the aspirating step of aspirating the cut debris D into the rotary body 20. Accordingly, the debris D can be quickly discharged outward of the blood vessel H, and the treatment time can be shortened.

Next, a medical device according to Modification Example 1 of the second exemplary embodiment will be described.

Figure 19A:
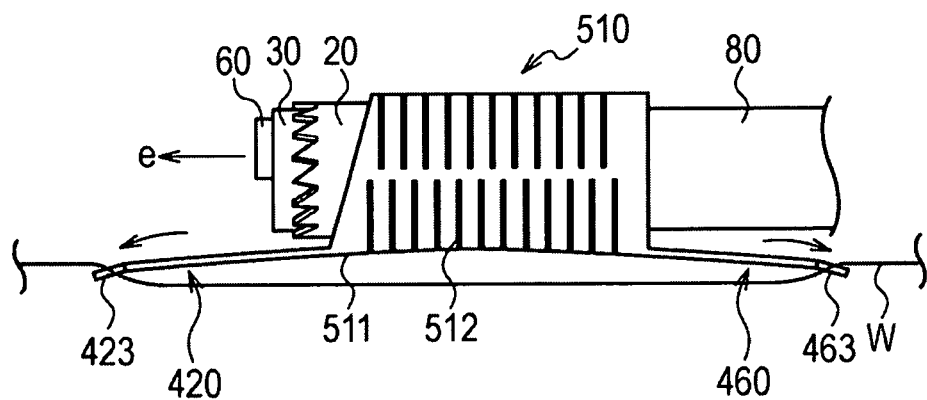
FIG. 19A is a view illustrating a distal member included in a medical device according to Modification Example 1 of the second exemplary embodiment.
Figure 19B:
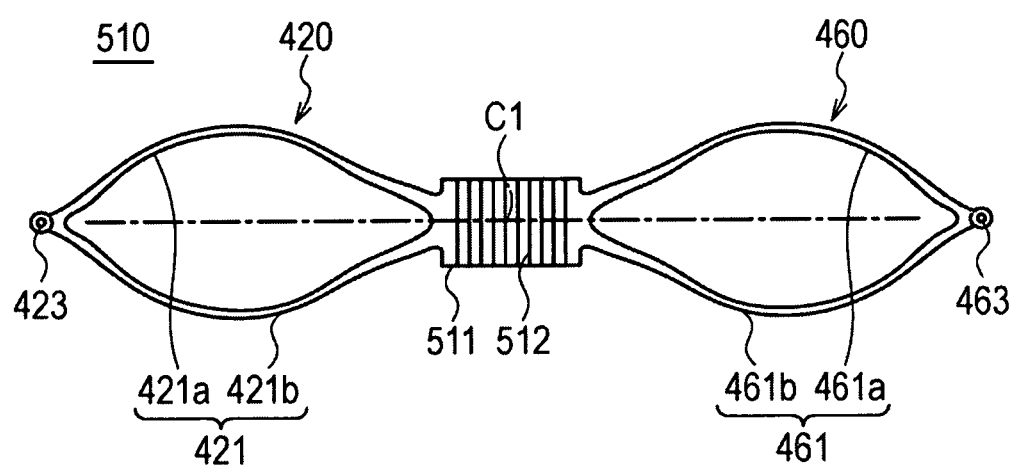
FIG. 19B is a bottom view illustrating the distal member included in the medical device according to Modification Example 1 of the second exemplary embodiment.

As illustrated in FIGS. 19A and 19B, a distal member 510 according to Modification Example 1 includes a link structure 512 for maintaining an orientation of the distal surface of the rotary body 20 indicated by an arrow e to be a predetermined direction. For example, the link structure 512 can be configured to include a slit disposed in a main body portion 511 of the distal member 510. The link structure 512 provides the distal member 510 with an added shape in which the central portion on the lower surface side of the distal member 510 is warped to the upper surface side. The warpage of the distal member 510 prevents the distal surface of the rotary body 20 inserted into the main body portion 511 from facing a lower side (lower side in FIG. 18A, which is the side away from the stenosed site S) from the position parallel to the running of the blood vessel H. In this manner, the cutting edge 21 can be prevented from coming into contact with the biological tissue other than the stenosed site S.

In this modification example, the guide wire insertion portion 423 is configured to include a through-hole disposed in the distal end of the support portion 420, and the guide wire insertion portion 463 is configured to include a through-hole disposed in the proximal end of the auxiliary support portion 460. Even in a case where the guide wire insertion portions 423 and 463 are configured to include the through-holes disposed in the respective support portions 420 and 460, the rotary body 20 can be smoothly delivered or moved using the guide wire W. In addition, the distal member 510 can be miniaturized compared to a case of using the hollow member such as the second site 422 and the second auxiliary site 462 which are illustrated in the above-described embodiment. Furthermore, it is possible to reduce the manufacturing cost by reducing the number of components.

Next, a medical device according to Modification Example 2 of the second exemplary embodiment will be described.

Figure 20A:
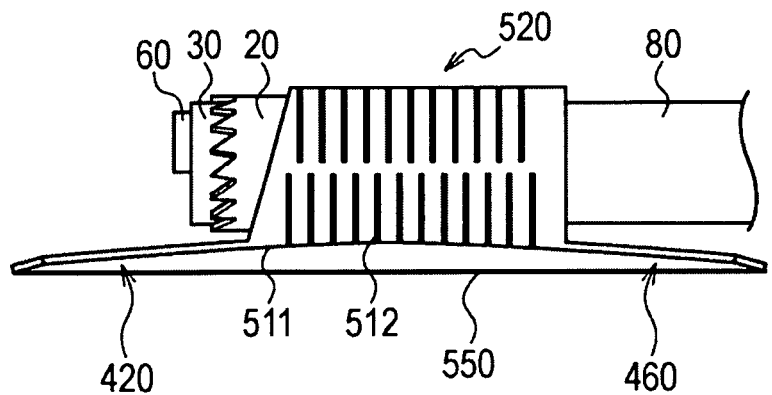
FIG. 20A is a view illustrating a distal member included in a medical device according to Modification Example 2 of the second exemplary embodiment.
Figure 20B:
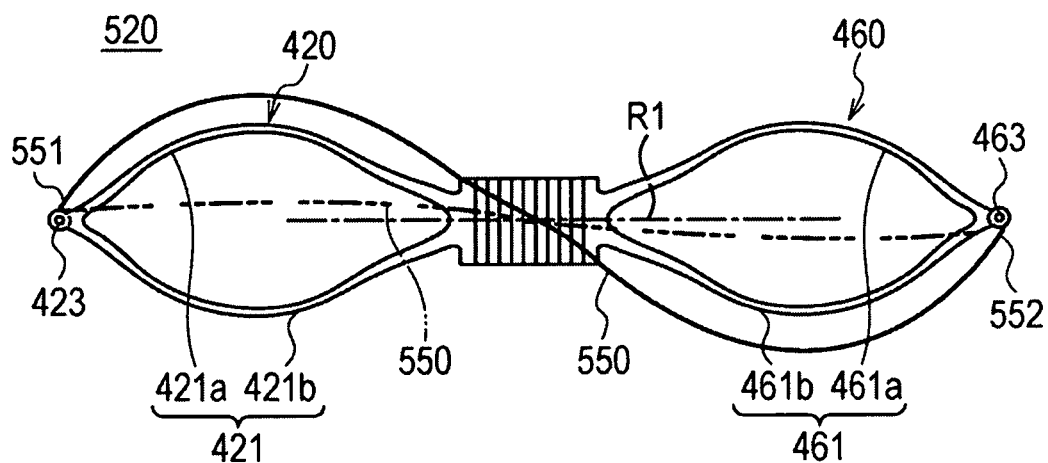
FIG. 20B is a bottom view illustrating the distal member included in the medical device according to Modification Example 2 of the second exemplary embodiment.

As illustrated in FIGS. 20A and 20B, a distal member 520 according to Modification Example 2 has an elastically deformable connection portion 550 connected to the support portion 420 and the auxiliary support portion 460.

In a state where the external force is not applied, the connection portion 550 has a shape protruding outward (upward-downward direction in FIG. 20B) from the support portion 420 and the auxiliary support portion 460 in the direction intersecting the extending direction of the rotary body 20.

In the connection portion 550, a distal portion 551 connected to the support portion 420 and a proximal portion 552 connected to the auxiliary support portion 460 respectively have shapes spreading in mutually symmetrical directions with respect to the rotary shaft R1 of the rotary body 20. In this modification example, the connection portion 550 has an S-shape in a plan view. However, the embodiment is not limited thereto. For example, the connection portion 550 may have a shape of a FIG. 8 in a plan view.

For example, the connection portion 550 can be configured to include an elastically deformable metal wire rod or a resin-made wire rod.

Figure 20C:
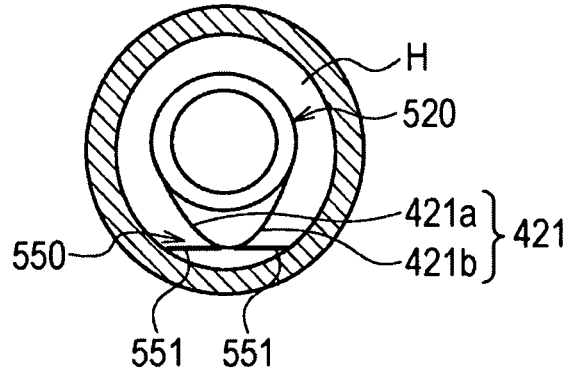
FIG. 20C is a cross-sectional view for describing an operation of the distal member included in the medical device according to Modification Example 2 of the second exemplary embodiment.

FIG. 20C schematically illustrates an axially orthogonal cross-section of the blood vessel H. For example, the illustrated blood vessel H is a flattened blood vessel H having a long dimension of the lumen in the upward-downward direction and a short dimension of the lumen in the rightward-leftward direction. If the distal member 520 is introduced into the blood vessel H, the connection portion 550 spreads in a minor axis direction (rightward-leftward direction in the drawing) of the blood vessel H. In this manner, the central position of the distal member 520, that is, the rotational center of the rotary body 20 is allowed to align with the central position of the blood vessel H in the minor axis direction. Therefore, it is possible to preferably prevent the cutting edge 21 of the rotary body 20 from coming into contact with the biological tissue other than the stenosed site S. The connection portion 550 is attached to the inner wall of the blood vessel H so as to increase a supporting force of the distal member 520 for supporting the blood vessel H. Accordingly, it is possible to prevent the orientation of the cutting edge 21 from being displaced while the cutting treatment is performed.

When the connection portion 550 is inserted into the guiding sheath whose inner diameter is smaller than the width (length in the upward-downward direction in FIG. 20B) of the connection portion 550 in an expanded state, the connection portion 550 is elastically deformed into a substantially linear shape as illustrated by a two-dot chain line in FIG. 20B. Accordingly, the width decreases. Therefore, the distal member 520 can also be smoothly moved inside the guiding sheath having a relatively small diameter.

Next, a medical device according to Modification Example 3 of the second exemplary embodiment will be described.

Figure 21B:
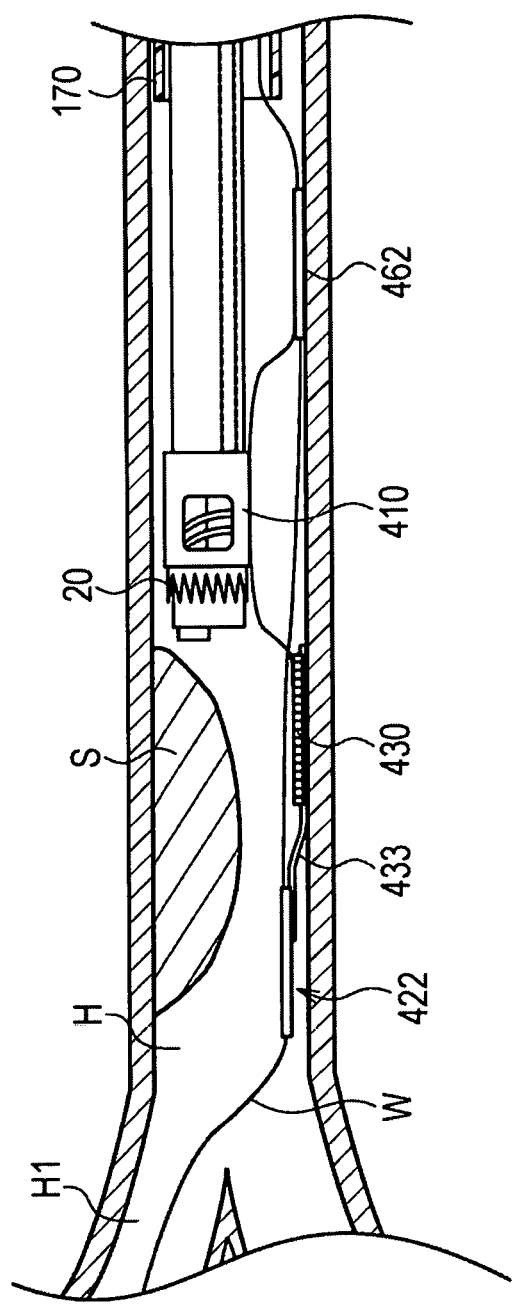
FIG. 21B is a cross-sectional view for describing an operation of the distal member included in the medical device according to Modification Example 3 of the second exemplary embodiment.

As illustrated in FIGS. 21A and 21B, in a distal member 530 according to Modification Example 3, the support portion 420 includes a third site 430 that extends between the first site 421 and the second site 422. The third site 430 is configured to include a member which is more flexible than the second site 422.

For example, the third site 430 can be configured to include a metal-made hollow member which has a slit and which can be curved. For example, the second site 422 can be configured to include a resin-made hollow member which is more rigid (harder) than the third site.

The third site 430 is connected to the second site 422 via a predetermined relay member 433. For example, the relay member 433 can be configured to include a resin-made coating member (for example, a known heat-shrinkable tube) which integrally interlocks the second site 422 and the third site 430 with each other. For example, the first site 421 and the third site 430 are appropriately connected to each other using an adhesive.

FIG. 21B illustrates a treatment example when using the distal member 530 according to Modification Example 3 in the blood vessel H where a branched blood vessel H1 is present on the distally located side (distal side) of the stenosed site S.

For example, if the guide wire W is introduced into the branched blood vessel H1 present on the distally located side of the stenosed site S and is greatly curved toward the branched blood vessel H1 side, the distal member 530 is affected by the curve of the guide wire W. Accordingly, an orientation, a posture, or a position of the distal member 530 may be corrected in the curved direction, in some cases. In addition, if the orientation of the distal member 530 is corrected, there is a possibility that the cutting edge 21 may be pushed against the vascular wall on the side having the stenosed site S by a force stronger than expected. In contrast, according to the distal member 530 of this modification example, the third site 430 located on the proximal side of the second site 422 is more flexible than the second site 422. Accordingly, since the second site 422 is curved, it is possible to restrain the rotary body 20 from being affected by the delivery the curved guide wire W. Therefore, when the guide wire W is used so as to deliver the rotary body 20 to a desired site, even if the guide wire W is greatly curved on the distal side, it is possible to prevent the cutting edge 21 from being directed in an unintended direction after being affected by the curve, or from being pushed against the vascular wall by the pushing force stronger than expected.

Next, a medical device according to Modification Example 4 of the second exemplary embodiment will be described.

Figure 22:
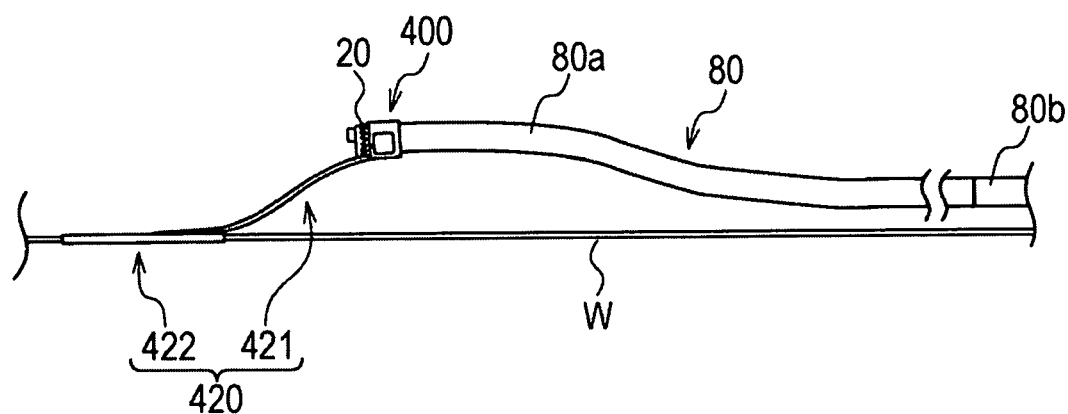
FIG. 22 is a view illustrating a medical device according to Modification Example 4 of the second exemplary embodiment.

Referring to FIG. 22, in this modification example, a shape memory member is used for the tube 80 connected to the proximal side of a distal member 400. The tube 80 is configured to raise the distal member 400 by being restored to a pre-memorized shape. The tube 80 is provided in advance with a curved shape which raises the distal member 400 in the height direction (upward direction in the drawing) when the tube 80 is pulled out from the guiding sheath used in the medical procedure.

For example, the tube 80 can be configured to include a hollow elongated shape memory member 80a, a heat-shrinkable tube (not illustrated) disposed to coat an outer surface thereof, and a hollow member 80b connected to the proximal side of the shape memory member 80a. In this modification example, heat is applied to the heat-shrinkable tube disposed so as to cover the shape memory member 80a. In this manner, the heat-shrinkable tube is integrally attached to the shape memory member 80a. For example, the hollow member 80b connected to the proximal side of the tube 80 can be configured to include a hollow metal tube.

For example, as the shape memory member 80a, a known shape memory alloy can be used. For example, as the shape memory alloy can be, a titanium alloy (Ti—Ni, Ti—Pd, and Ti—Nb—Sn) or a copper alloy can be used. In addition, for example, as the shape memory member 80a, a known shape memory resin (shape memory polymer) can be used. For example, as the shape memory resin, acrylic resin, toluene copolymer, polynorbornene, styrene-butadiene copolymer, and polyurethane can be used.

Figure 23:
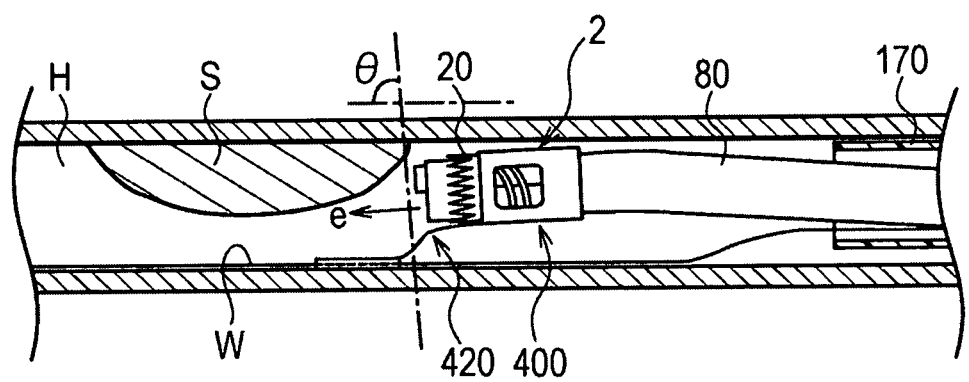
FIG. 23 is a cross-sectional view for describing an operation of the medical device according to the second exemplary embodiment.

In the medical procedure using the medical device 2 including a raising mechanism (support portion 420) extending from the distal member 400 to the distal side, even in a case where the treatment is performed in a state where the orientation of the cutting edge 21 is inclined in the downward direction (for example, an inclination angle θ is 90° or smaller) as illustrated in FIG. 23, the cutting edge 21 and the lower surface of the vascular wall are separated from each other by the support portion 420. Therefore, it is possible to prevent the cutting edge 21 from inadvertently coming into contact with the vascular wall. Accordingly, the treatment can be performed on the stenosed site S while the vascular wall is more preferably prevented from being damaged.

Next, a medical device according to Modification Example 5 of the second exemplary embodiment will be described.

Figure 24A:
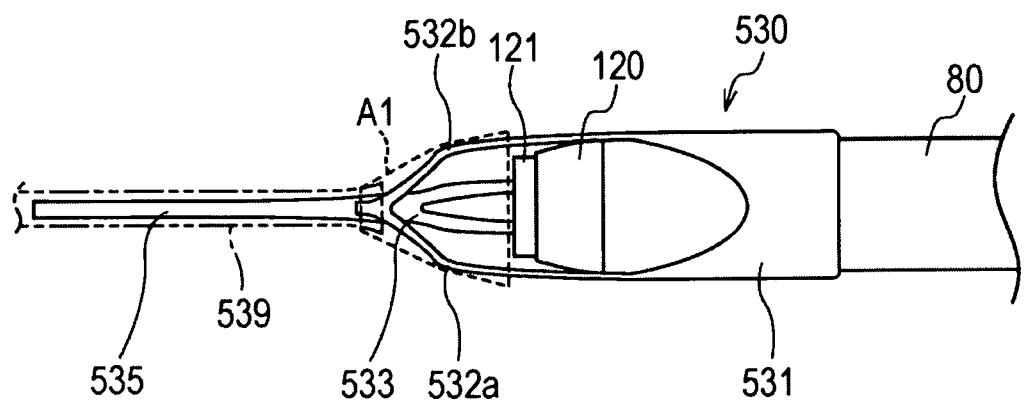
FIG. 24A is a view illustrating a distal member included in a medical device according to Modification Example 5 of the second exemplary embodiment.
Figure 24B:
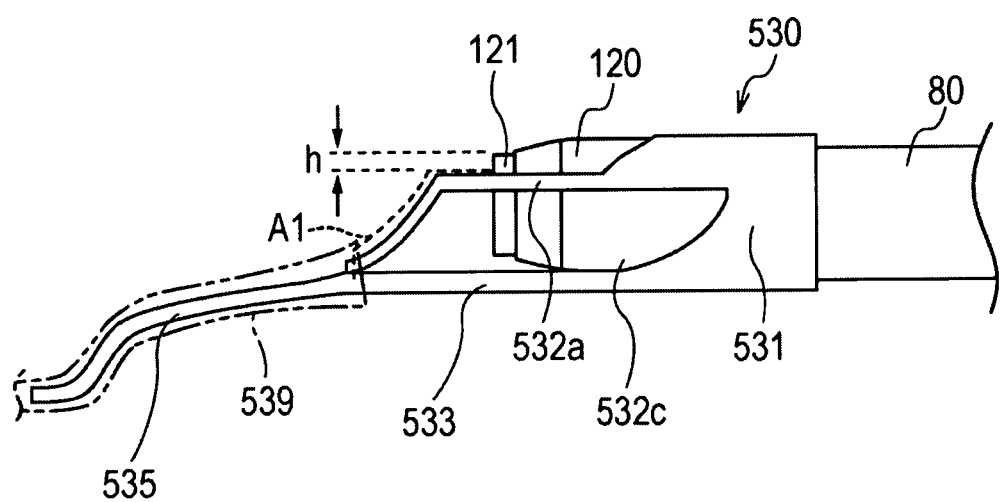
FIG. 24B is a side view of the distal member included in the medical device according to Modification Example 5 of the second exemplary embodiment.

As illustrated in FIGS. 24A and 24B, a distal member 530 illustrated in this modification example has a main body portion 531 into which the rotary body 120 including the cutting edge 121 is inserted, side surface portions 532a and 532b extending from the main body portion 531 toward the distal side, a bottom surface portion 533 disposed on the bottom surface side of the cutting edge 121, and a support portion 535 which supports the rotary body 120 on the distal side.

A gap between the side surface portion 532a and the side surface portion 532b gradually decreases toward the distal side. In addition, the distal side of the respective side surface portions 532a and 532b is inclined toward the bottom surface portion 533 side. An opening portion 532c is disposed on the side surface of the respective side surface portions 532a and 532b.

The rotary body 120 is disposed in a state of being interposed between the respective side surface portions 532a and 532b. Accordingly, the rotary body does not inadvertently protrude therefrom. Even in a case where the rotary body 120 is damaged, the rotary body 120 is held by the respective side surface portions 532a and 532b and the bottom surface portion 533. Therefore, the rotary body 120 is prevented from falling. Furthermore, the respective side surface portions 532a and 532b prevent the rotary body 120 from inadvertently protruding on the distal side of the rotary body 120, thereby preventing the rotary body 120 from excessively entering the stenosed site S. In this manner, it is possible to preferably prevent the normal tissue from being damaged by the cutting edge 121. In addition, the cutting edge 121 applies the cutting force to the stenosed site S from the side surface of the main body portion 531 via the opening portion 532c. Therefore, the stenosed site S can be efficiently cut.

On the distal side beyond the cutting edge 121 of the rotary body 120, a guide surface A1 is formed by the distal surface of the respective side surface portions 532a and 532b. The guide surface A1 supports the rotary body 120 with respect to the stenosed site S while the treatment is performed by bringing the cutting edge 121 into contact with the stenosed site S, thereby preventing the cutting edge 121 and the rotary body 120 from being separated from the stenosed site S. In this manner, the cutting edge 121 is prevented from moving outward of the biological lumen (for example, in a direction toward the lower surface of the blood vessel H which is illustrated in FIG. 20C). In addition, the guide surface A1 limits a range in the height direction where the cutting edge 121 applies the cutting force to a range of a portion where the cutting edge 121 is exposed from the respective side surface portions 532a and 532b (range of a height h illustrated in FIG. 24B). Therefore, even in a case where the cutting is performed after the cutting edge 121 inadvertently comes into contact with a site other than the stenosed site S, and in a case where the tube wall of the biological lumen is thicker than the height h, it is possible to sufficiently suppress a disadvantage that the biological lumen may be perforated.

For example, as illustrated, the support portion 535 can be configured to include a single member whose width gradually decreases toward the distal side and whose distal side is curved downward. Although not illustrated, the second site 422 (refer to FIGS. 15A and 15B) having the guide wire insertion portion (lumen) 423 can be appropriately attached to the support portion 535. For example, the second site 422 can be disposed on the distal side of the guide surface A1. In a case where the second site 422 is provided, the support portion 535 and the second site 422 are coated with a resin-made coating member (for example, a known heat-shrinkable tube) 539 as illustrated in FIG. 24B, and the coating member 539 can be thermally shrunk so that all of these are integrally interlocked with each other. For example, as the coating member 539, it is possible to use a hollow member configured to include fluorocarbon resin such as ethylene tetrafluoro ethylene copolymer (ETFE) and polytetrafluoroethylene (PTFE), polyolefin such as polyethylene (PE) and polypropylene (PP), polyamide, polyester, or polyurethane.

Figure 25:
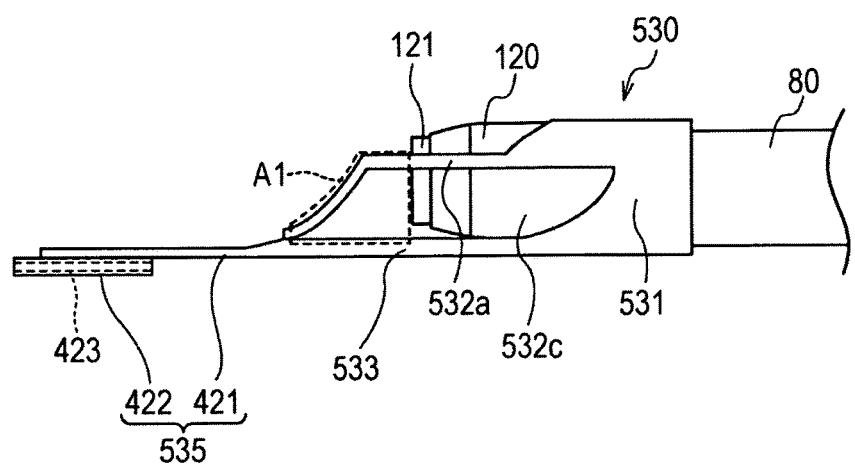
FIG. 25 is a view illustrating a medical device according to Modification Example 6 of the second exemplary embodiment.

As illustrated in the respective modification examples, a specific configuration of the support portion is not particularly limited, as long as the support portion provided with the function to raise the rotary body has a structure which supports the rotary body inside the lumen of the blood vessel, and in which the distance from the rotary body is variable. For example, as in Modification Example 6 illustrated in FIG. 25, the support portion 535 can be configured to include the first site 421 substantially linearly extending in the axial direction, and the second site 422 disposed in the distal portion of the first site 421 and having the guide wire insertion portion 423. Even in a case where the first site 421 is substantially linearly disposed rather than a curved shape as in the support portion 535, if the second site 422 comes into contact with the inner wall of the biological lumen, the first site 421 is supported on the inner wall of the biological lumen by the contact. As a result, the rotary body 120 together with the first site 421 is raised, and the position of the rotary body 120 is adjusted in the height direction of the biological lumen. The first site 421 and the second site 422 can be integrally interlocked with each other using a resin-made coating member (for example, a known heat-shrinkable tube).

Hitherto, the medical device and the treatment method according to the disclosure herein have been described with reference to the exemplary embodiments and modifications thereto. However, the present invention is not limited to only the contents described in the embodiments. The present invention can be appropriately modified, based on the appended claims.

For example, each configuration described in the first exemplary embodiment and the modification examples and each configuration described in the second exemplary embodiment and the modification examples can be appropriately combined with each other, as long as the combined configuration is not contradictory to the description in the appended claims, and the disclosure is not limited to the combinations described herein.

For example, the biological lumen serving as an application target of the medical device and the treatment method is not limited to the blood vessel. For example, the disclosure may be applicable to a vessel, a ureter, a bile duct, a fallopian tube, or a hepatic duct. In addition, the object serving as the cutting target is not limited to the stenosed site.

The structure of each portion or the arrangement of the members in the medical device described in the exemplary embodiments can be appropriately modified. Using the additional members described with reference to the drawing can be appropriately omitted, and using other additional members can be appropriately omitted. Similarly, each step relating to the treatment method or each device used for the treatment can be appropriately modified.

The detailed description above describes features, characteristics and operational aspects of embodiments of a medical device and treatment method representing examples of the medical device and treatment method disclosed herein. The disclosure and the present invention are not limited, however, to the precise embodiments and variations described. Various changes, modifications and equivalents could be effected by one skilled in the art without departing from the spirit and scope of the disclosure as defined in the appended claims. It is expressly intended that all such changes, modifications and equivalents which fall within the scope of the claims are embraced by the claims.

What is claimed is:

1. A medical device for cutting an object inside a biological lumen, comprising:
   a rotatable elongated member;
   a rotary body that includes a cutting edge for applying a cutting force to the object, and that is disposed on a distal side of the elongated member so as to be rotated in conjunction with rotation of the elongated member, the rotary body having a hollow cylindrical shape;
   a switching portion whose distal end is disposed at a position protruding from the cutting edge;
   a holding portion configured to hold the switching portion so as to move the switching portion on the same plane as the cutting edge or to a position away from the object beyond the cutting edge in accordance with a pushing force, when the switching portion is pushed against the object; and
   an aspiration lumen configured to aspirate at least a portion of the object after the object has been cut,
   wherein the switching portion, the holding portion and the aspiration lumen are disposed in the rotary body.

2. The medical device according to claim 1,
   wherein a main body portion having a lumen for communicating with an interior of the rotary body is disposed in a proximal end of the rotary body, and
   the holding portion is stretchable and deformable along an extending direction of the main body portion.

3. The medical device according to claim 2,
   wherein the main body portion has a tubular shape including a distal opening portion, a proximal opening portion, and the lumen is linked to the distal opening portion and the proximal opening portion,
   at least a portion of the holding portion is inserted into the main body portion, and
   the switching portion is movable in an inward-outward direction of the main body portion by stretchable deformation of the holding portion.

4. The medical device according to claim 2,
   wherein the holding portion is configured to include a hollow spring, and
   the switching portion is integrally disposed in a distal portion of the holding portion.

5. The medical device according to claim 4,
   further comprising a side hole through which an interior and an exterior of the holding portion communicate with each other, the side hole being disposed on a side surface of the main body portion.

6. The medical device according to claim 2,
   further comprising a cutting portion disposed in a distal end of the switching portion, the cutting portion and the cutting edge of the rotary body together applying the cutting force to the object.

7. The medical device according to claim 1, further comprising:
   a cutting assistance portion that is disposed in the rotary body, and that protrudes to a distal side beyond the cutting edge so as to assist cutting performed by the cutting edge.

8. The medical device according to claim 7,
   wherein the cutting assistance portion has a substantially U-shape.

9. The medical device according to claim 1,
   wherein the cutting edge includes a tapered blade surface whose thickness is thinned toward a distal side of the rotary body.

10. The medical device according to claim 1,
    wherein the cutting edge includes a blade surface which is cut out in an uneven shape.

11. The medical device according to claim 1,
    further comprising a cutting portion disposed in a distal end of the switching portion, the cutting portion and the cutting edge of the rotary body together applying the cutting force to the object.

12. The medical device according to claim 1, wherein the aspiration lumen extends through the holding portion.

13. The medical device according to claim 12, wherein the holding portion is attached to an inner surface of the rotary body.

14. A treatment method for cutting an object inside a biological lumen, comprising:
moving a switching portion and bringing the switching portion into a state of protruding to a distal side of a rotary body including a cutting edge for applying a cutting force to the object, the rotary body having a hollow cylindrical shape, and pushing the switching portion against the object so as to move the switching portion on the same plane as the cutting edge or to a position away from the object beyond the cutting edge;
cutting the object by causing the cutting edge to cut the object in a state where the switching portion is moved; and
aspirating at least a portion of the object through an aspiration lumen after the object has been cut,
wherein moving the switching portion is performed by causing a holding portion for holding the switching portion to be contracted and deformed along an extending direction of a main body portion including a lumen for communicating with an interior of the rotary body, and
wherein the switching portion, the holding portion and the aspiration lumen are disposed in the rotary body.

15. The treatment method according to claim 14,
wherein at least a portion of the holding portion is disposed inside the main body portion, and
the switching portion is movable in an inward-outward direction of the main body portion by stretchable deformation of the holding portion.

16. The treatment method according to claim 14,
wherein the holding portion is a hollow spring, and
the switching portion is integrally disposed in a distal portion of the holding portion.

17. The treatment method according to claim 16, further comprising:
introducing the cut object into the main body portion and into the holding portion via a side hole disposed on a side surface of the main body portion.

18. The treatment method according to claim 14,
wherein the cutting step includes cutting the object while causing a cutting assistance portion disposed in the rotary body to assist cutting performed by the cutting edge.

19. The treatment method according to claim 14, further comprising:
cutting the object by using a blade surface disposed in a distal end of the switching portion.

* * * * *